US012658300B2

(12) United States Patent
Takashima et al.

(10) Patent No.:   US 12,658,300 B2
(45) Date of Patent:     Jun. 16, 2026

(54) DRUG MANAGEMENT SYSTEM, CLOUD SERVER, DRUG PACKAGING APPARATUS, DRUG PACKAGE AUDITING APPARATUS, PACKAGING BAG, AND DRUG MANAGEMENT METHOD

(71) Applicant: FUJIFILM Medical Co., Ltd., Tokyo (JP)

(72) Inventors: Masanobu Takashima, Ashigarakami-gun (JP); Yoshiaki Ishimaru, Ashigarakami-gun (JP); Tetsuya Takamori, Ashigarakami-gun (JP); Manabu Hisamoto, Yokohama (JP)

(73) Assignee: FUJIFILM MEDICAL CO., LTD., Tokyo (JP)

( * ) Notice: Subject to any disclaimer, the term of this patent is extended or adjusted under 35 U.S.C. 154(b) by 1080 days.

(21) Appl. No.: 16/698,399

(22) Filed: Nov. 27, 2019

(65) Prior Publication Data

US 2020/0098462 A1      Mar. 26, 2020

Related U.S. Application Data

(63) Continuation of application No. PCT/JP2018/018379, filed on May 11, 2018.

(30) Foreign Application Priority Data

May 31, 2017   (JP) ................................. 2017-108293
May 8, 2018    (JP) ................................. 2018-090131

(51) Int. Cl.
*G16H 20/13* (2018.01)
*G06K 7/10* (2006.01)
(Continued)

(52) U.S. Cl.
CPC ......... *G16H 20/13* (2018.01); *G06K 7/10445* (2013.01); *G06T 7/001* (2013.01); *G07F 17/0092* (2013.01); *G16H 10/60* (2018.01)

(58) Field of Classification Search
None
See application file for complete search history.

(56) References Cited

U.S. PATENT DOCUMENTS 9,272,796 B1      3/2016  Chudy
2005/0240305 A1*  10/2005  Bogash ..................... A61J 7/04
                                                 700/242
(Continued)

FOREIGN PATENT DOCUMENTS

CN      105307622 A      2/2016
JP       9-299448 A      11/1997
(Continued)

OTHER PUBLICATIONS

Venkov, Ventsislav, and Rosen Ivanov. "Cloud-based system for real time medication monitoring." Proceedings of the 17th international conference on computer systems and technologies 2016. 2016. (Year: 2016).*
(Continued)

*Primary Examiner* — Lena Najarian
(74) *Attorney, Agent, or Firm* — Birch, Stewart, Kolasch & Birch, LLP

(57)       ABSTRACT

The present invention can ensure traceability of packaged drugs. A label printer of a drug packaging apparatus provided in a dispensing pharmacy or the like prints unique identification information, which is only one in the world issued by a numbering server on a package basis, on a label, and attaches the label to a packaging bag in which drugs are packaged by a drug packing unit. The dispensing pharmacy uploads at least drug information of the packaged drugs, to which the unique identification information is added, to a
(Continued)

cloud server in association with the unique identification information. The cloud server unitarily manages the drug information of the packaged drugs uploaded from the dispensing pharmacy or the like in association with the unique identification information. The packaged drugs can be traced by making inquiries to the cloud server based on the unique identification information added to the packaging bag.

13 Claims, 16 Drawing Sheets

(51) Int. Cl.
| | | |
|---|---|---|
| *G06T 7/00* | (2017.01) | |
| *G07F 17/00* | (2006.01) | |
| *G16H 10/60* | (2018.01) | |

(56) References Cited

U.S. PATENT DOCUMENTS

| | | | | |
|---|---|---|---|---|
| 2007/0265730 A1 * | 11/2007 | Greyshock | .......... | G07F 17/0092 |
| | | | | 700/236 |
| 2010/0239169 A1 * | 9/2010 | Braun | .................... | G01B 11/26 |
| | | | | 382/190 |
| 2012/0111934 A1 | 5/2012 | Herzig | | |
| 2012/0145739 A1 * | 6/2012 | Doyle | ................. | B65D 75/327 |
| | | | | 225/56 |
| 2013/0222116 A1 * | 8/2013 | Barry, III | ............... | G16H 40/20 |
| | | | | 340/10.1 |
| 2016/0104277 A1 | 4/2016 | Takamori | | |
| 2017/0065485 A1 * | 3/2017 | Trower | .................. | B65D 75/54 |
| 2017/0076065 A1 * | 3/2017 | Darr | ....................... | G16H 70/40 |

FOREIGN PATENT DOCUMENTS

| | | | | |
|---|---|---|---|---|
| JP | 2002-123607 A | | 4/2002 | |
| JP | 2007-73074 A | | 3/2007 | |
| JP | 2013066533 A | * | 4/2013 | |
| JP | 2016-24821 A | | 2/2016 | |
| JP | 2016-126361 A | | 7/2016 | |
| JP | 2016-179161 A | | 10/2016 | |
| TW | 201222308 A1 | | 6/2012 | |
| WO | WO 2015/040366 A1 | | 3/2015 | |

OTHER PUBLICATIONS

Japanese Notice of Reasons for Refusal for corresponding Japanese Application No. 2021-100287, dated Aug. 4, 2022, with an English translation.
Japanese Notice of Reasons for Refusal for corresponding Japanese Application No. 2019-522074, dated Jan. 27, 2021, with an English translation.
Japanese Notice of Reasons for Refusal for corresponding Japanese Application No. 2019-522074, dated Apr. 14, 2021, with an English translation.
Extended European Search Report dated Mar. 9, 2020, for European Application No. 18810389.9.
International Preliminary Report on Patentability, dated Dec. 3, 2019, and English translation of the Written Opinion of the International Searching Authority, dated Aug. 14, 2018, (Forms PCT/IB/373, and PCT/ISA/237) for International Application No. PCT/JP2018/018379.
European Communication pursuant to Article 94(3) EPC for corresponding European Application No. 18810389.9, dated Mar. 3, 2023.
Chinese Office Action and Search Report for corresponding Chinese Application No. 201880029046.2, dated Oct. 31, 2022, with an English translation.
Japanese Notice of Reasons for Refusal for corresponding Japanese Application No. 2021-100287, dated Nov. 18, 2022, with an English translation.
Chinese Office Action for corresponding Chinese Application No. 201880029046.2, dated Mar. 21, 2023, with an English translation.
Chinese Office Action dated May 23, 2023 for corresponding Application No. 201880029046.2 with an English translation.
European Communication pursuant to Article 94(3) EPC for counterpart European Application No. 18 810 389.9, dated May 3, 2024.
European Communication pursuant to Article 94(3) EPC for counterpart European Application No. 18 810 389.9, dated Mar. 11, 2026.
Chinese Reexamination Notification for counterpart Chinese Application No. 201880029046.2, dated Mar. 27, 2026, with English translation.
Chinese Reexamination Decision for counterpart Chinese Application No. 201880029046.2, dated Apr. 29, 2026, with English translation.

* cited by examiner

FIG.3

| UNIQUE ID | DRUG INFORMATION | | PRESCRIPTION DATE | PATIENT INFORMATION | HOSPITAL INFORMATION | FACILITY INFORMATION | ..... |
| | DRUG CHARACTER INFORMATION | DRUG IMAGE | | | | | |
| AxxxZOxxOOxxx1 | CAPSULE A 1 TABLET TABLET B 10mg 1 TABLET ..... | | 2016/07/26 | NAME: TARO FUJI SEX: MALE AGE: 30 | PRESCRIPTION: MINATO CLINIC | FACILITY: MINATO PHARMACY | ..... |
| AxxxZOxxOOxxx2 | | | ..... | ..... | ..... | ..... | ..... |

Figure 6:
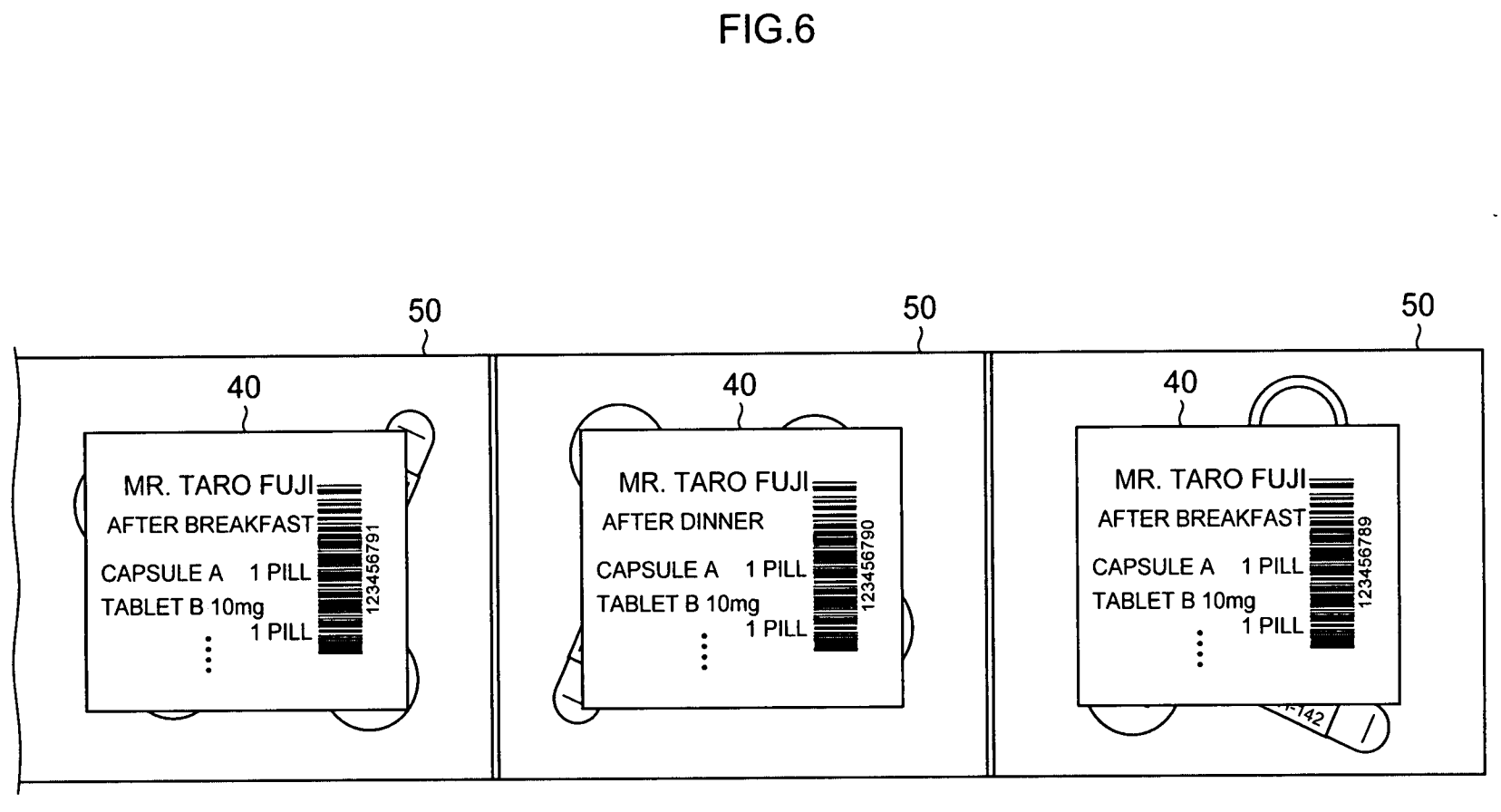

MR. TARO FUJI
AFTER BREAKFAST

CAPSULE A    1 PILL
TABLET B 10mg
                1 PILL
        · · · ·

123456789

42

50

40

MR. TARO FUJI
AFTER DINNER

CAPSULE A    1 PILL
TABLET B 10mg
                1 PILL
        · · · ·

123456790

50

40

MR. TARO FUJI
AFTER BREAKFAST

CAPSULE A    1 PILL
TABLET B 10mg
                1 PILL
        · · · ·

Figure 12:
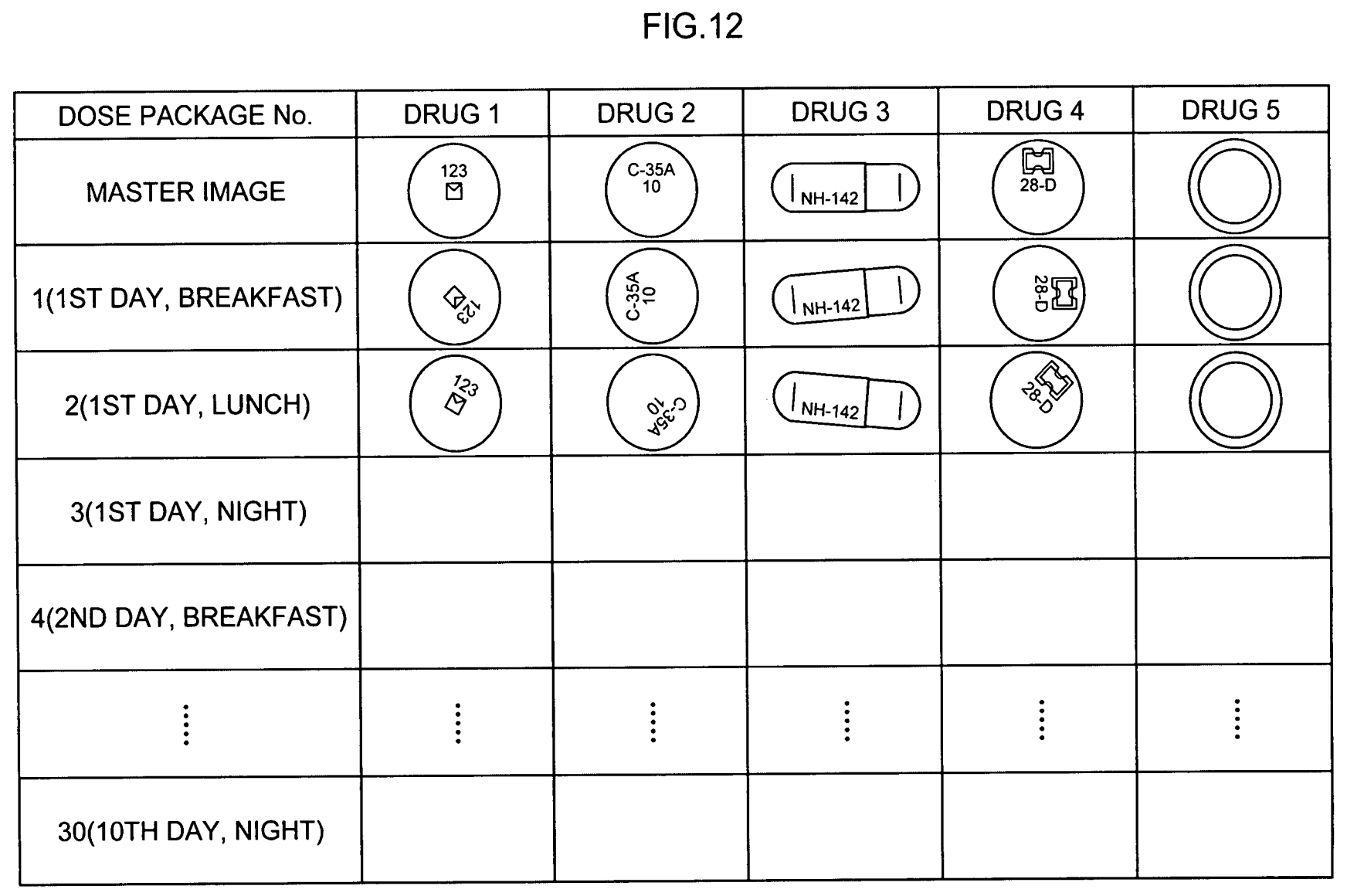

| DOSE PACKAGE No. | DRUG 1 | DRUG 2 | DRUG 3 | DRUG 4 | DRUG 5 |
|---|---|---|---|---|---|
| MASTER IMAGE | 123 | C-35A 10 | NH-142 | 28-D | ◯ |
| 1(1ST DAY, BREAKFAST) | 123 | C-35A 10 | NH-142 | 28-D | ◯ |
| 2(1ST DAY, LUNCH) | 123 | C-35A 10 | NH-142 | 28-D | ◯ |
| 3(1ST DAY, NIGHT) | | | | | |
| 4(2ND DAY, BREAKFAST) | | | | | |
| 30(10TH DAY, NIGHT) | ..... | ..... | ..... | ..... | ..... |

DRUG MANAGEMENT SYSTEM, CLOUD SERVER, DRUG PACKAGING APPARATUS, DRUG PACKAGE AUDITING APPARATUS, PACKAGING BAG, AND DRUG MANAGEMENT METHOD

CROSS-REFERENCE TO RELATED APPLICATIONS

The present application is a Continuation of PCT International Application No. PCT/JP2018/018379 filed on May 11, 2018 claiming priorities under 35 U.S.C § 119(a) to Japanese Patent Application No. 2017-108293 filed on May 31, 2017 and Japanese Patent Application No. 2018-090131 filed on May 8, 2018. Each of the above applications is hereby expressly incorporated by reference, in its entirety, into the present application.

BACKGROUND OF THE INVENTION

1. Field of the Invention

The present invention relates to a drug management system, a cloud server, a drug packaging apparatus, a drug package auditing apparatus, a packaging bag, and a drug management method, and more particularly to a technique for unitarily managing packaged drugs.

2. Description of the Related Art

In recent years, there are increasing number of "one-dose package dispensation" in which a plurality of drugs to be taken by a recipient at each dose are packaged in a single packaging bag for each dose.

Japanese Patent Application Laid-Open No. 2016-179161 (hereinafter referred to as "PTL 1") proposes a drug distribution support system capable of supporting administration of a drug package without omission when there are a plurality of packaged drugs (drug packages) for one administration time.

The drug distribution support system disclosed in PTL 1 includes a drug packaging device and a printer of a pharmacy, a drug distribution support device and a mobile terminal of a long-term care health facility (elderly health facility), and the like.

The drug packaging device of the pharmacy performs one-dose package dispensation according to prescription data for residents in the elderly health facility and prints a drug package code on each drug package using a printer. Here, the drug package code is identification data by which the drug package can be identified, and is specifically a one-dimensional code or a two-dimensional code including information of a drug package number, a resident ID (identification), a resident's name, and a drug administration time, for example.

The drug distribution support device of the elderly health facility includes a data storage unit for storing a resident master including information of a resident ID, a resident's name, a face image, a medical history, or a drug history on a resident who has moved into the elderly health facility. A person in charge of drug distribution at the elderly health facility can read the drug package code printed on the drug package using his/her mobile terminal to acquire information corresponding to the drug package code from the drug distribution support device, collate the resident indicated by the drug package code by displaying the resident's name and the face image on the screen of the mobile terminal, and confirm a drug administration time. Thus, it is possible for the person in charge of drug distribution to efficiently perform drug distribution work and suppress administration error in the drug distribution work.

CITATION LIST

PTL 1: Japanese Patent Application Laid-Open No. 2016-179161

SUMMARY OF THE INVENTION

The drug distribution support system disclosed in PTL 1 prints the drug package code on the packaged drugs (drug package) and makes it possible to identify the drug packages one by one, but the drug package code is a one-dimensional code or a two-dimensional code including information of a drug package number, a resident ID, a resident name, and a drug administration time, for example. The drug package number is a preset three-digit number including a machine serial number that can identify the drug distribution device, and a drug type number that can identify the drug package, but is not a unique ID that uniquely specifies the drug package.

In addition, the drug distribution support system disclosed in PTL 1 is a system that supports drug distribution for a plurality of recipients represented in the elderly health facility, but does not enable traceability regarding drug information of the packaged drugs (drug package) that have been packaged.

The present invention has been made in consideration of such circumstances, and an object thereof is to provide a drug management system, a cloud server, a drug packaging apparatus, a drug package auditing apparatus, a packaging bag, and a drug management method which are capable of easily acquiring drug information of packaged drugs which have been one-dose packaged, regardless of time and place and further enabling traceability even for packaged drugs that have been respectively one-dose packaged at unspecified facilities.

In order to achieve the above object, an aspect of the present invention is drug management system which unitarily manages packaged drugs packaged by one or more facilities, on a package basis, the drug management system comprising: a cloud server configured to manage, in association with each other, unique identification information for uniquely specifying the packaged drugs on a package basis and drug information of the packaged drugs corresponding to at least the unique identification information; a drug packing unit provided in the one or more facilities and configured to put and package drugs to be taken in one dose according to prescription data in a packaging bag; a numbering unit provided in the cloud server or provided in the one or more facilities, and configured to issue the unique identification information; an information adding unit configured to add the unique identification information issued by the numbering unit to the packaging bag; and a communication unit configured to upload at least drug information of the packaged drug contained in the packaging bag in association with the unique identification information, to the cloud server.

According to the aspect of the present invention, the information adding unit of the one or more facilities adds unique identification information which is only one in the world issued by the numbering unit on a package basis, to the packaging bag including in which the drugs are packaged by the drug packing unit. The one or more facilities uploads at least the drug information of the packaged drugs to which the unique identification information is added, to the cloud server in association with the unique identification information. The cloud server unitarily manages the drug information of the packaged drugs uploaded from the one or more facilities in association with the unique identification information. Thus, even when the identity (the drug information of the drugs contained in the packaging bag) of the packaged drugs packaged by a facility such as a pharmacy is unknown, the identity of the packaged drugs can be acquired by making inquiries to the cloud server based on the unique identification information added to the packaging bag. Therefore, the packaged drug can be traced.

In the drug management system according to another aspect of the present invention, it is preferable that the information adding unit adds the unique identification information or a barcode indicating the unique identification information to the packaging bag; or attaches to the packaging bag, a label on which the unique identification information or the barcode indicating the unique identification information is added; or records the unique identification information on an electronic tag attached to the packaging bag. Here, the unique identification information or the barcode indicating the unique identification information may be encrypted. Further, the barcode may be a one-dimensional barcode, or a two-dimensional barcode.

In the drug management system according to further another aspect of the present invention, it is preferable that the information adding unit further adds, among patient information, a drug administration time and drug information of the packaged drugs, at least the drug administration time to the packaging bag. This is because the drugs contained in the packaged drug may differ depending on the drug administration time such as after breakfast and after lunch, and because a number of administration may differ such as twice a day and three times a day.

In the drug management system according to further another aspect of the present invention, it is preferable that the communication unit uploads information described in the prescription data in association with the unique identification information, to the cloud server, and the cloud server further manages the information described in the prescription data in association with the unique identification information. The information described in the prescription data includes, for example, information of prescription date, patient information, a prescription hospital and a doctor, in addition to the drug information.

In the drug management system according to further another aspect of the present invention, it is preferable that the drug management system further includes: an imaging unit configured to capture an image of the packaged drugs before or after the drugs are put and packaged in the packaging bag; and a drug auditing unit configured to support a pharmacist to confirm whether the packaged drugs are drugs corresponding to the prescription data based on the image of the packaged drugs captured by the imaging unit. The pharmacist can easily confirm the details (for example, imprinting of the drug) of the packaged drugs by watching the image of the packaged drugs imaged by the imaging unit, as compared with the case of directly watching the drugs. Or, when the drug auditing unit automatically inspects the packaged drug based on the image, the pharmacist can use the audit result from the drug auditing unit so that the pharmacist can perform the audit work more efficiently with less audit errors.

In the drug management system according to further another aspect of the present invention, it is preferable that the communication unit uploads, when the pharmacist confirms that the packaged drugs are drugs corresponding to the prescription data, drug character or symbol information and the image used for audit in the drug auditing unit in association with the unique identification information, as drug information of the packaged drugs, to the cloud server, and the cloud server manages the drug information and image of the packaged drugs in association with the unique identification information. Thus, the image used for the audit as well as the drug character or the symbol information of the packaged drug can be confirmed, and ensure traceability of the drug audit.

In the drug management system according to further another aspect of the present invention, it is preferable that the drug management system further includes a client terminal configured to be capable of accessing the cloud server, wherein the client terminal includes: an information reading unit configured to read the unique identification information added to the packaging bag; and a drug information acquiring unit configured to acquire, from the cloud server, at least the drug information of the packaged drugs contained in the packaging bag, based on the unique identification information read by the information reading unit.

Accessing persons including doctors, pharmacists, nurses, recipients, and other users can use his/her client terminal to read the unique identification information added to the packaging bag. Therefore, they can easily acquire the drug information or the like of the packaged drugs contained in the packaging bag, from the cloud server. The cloud server preferably restricts browsing of personal information and the like depending on the accessing persons.

In the drug management system according to further another aspect of the present invention, it is preferable that the unique identification information is a GS1 identification code. The GS1 identification code is an international standard identification code defined by GS1 (General Specifications One).

A cloud server according to further another aspect of the present invention constitutes (is included in) the drug management system described above.

Another aspect of the present invention is a drug packaging apparatus provided to one or more facilities, the drug packaging apparatus including: a drug packing unit configured to put and package drugs to be taken in one dose according to prescription data in a packaging bag; a unique identification information acquiring unit configured to acquire, from a numbering unit configured to issue unique identification information for uniquely specifying packaged drugs packaged by the one or more facilities on a package basis, the unique identification information; an information adding unit configured to add the unique identification information acquired by the unique identification information acquiring unit to the packaging bag; and a communication unit configured to upload at least drug information of the packaged drugs contained in the packaging bag in association with the unique identification information, to a cloud server configured to unitarily manage packaged drugs packaged by the one or more facilities on a package basis.

The drug packaging apparatus according to further another aspect of the present invention puts and packages the drugs to be taken in one dose according to the prescription data in the packaging bag, and adds the unique identification information to the packaging bag. The numbering unit which issues the unique identification information may be provided to the cloud server, or may be provided to each drug packaging apparatus. The communication unit of the drug packaging apparatus uploads the drug information of the packaged drugs contained in the packaging bag in association with the unique identification information to the cloud server. The packaged drugs can be traced by the cloud server that unitarily manages the packaged drug on a package basis, in association with the unique identification information.

Further another aspect of the present invention is a drug packaging apparatus provided to one or more facilities, the drug packaging apparatus including: a first drug packaging apparatus including a drug packing unit configured to put and package drugs to be taken in one dose according to prescription data in a packaging bag; and a numbering device configured to issue unique identification information for uniquely specifying packaged drugs packaged by the drug packaging apparatus, on a package basis, wherein at least one of the drug packaging apparatus and the numbering device includes: an information adding unit configured to add the unique identification information issued from the numbering device for the packaged drugs packaged by the drug packaging apparatus, to the packaging bag; a communication unit configured to upload, in association with the unique identification information, at least drug information of the packaged drugs contained in the packaging bag to the cloud server that unitarily manages packaged drugs packaged by the one or more facilities, on a package basis.

The drug packaging apparatus according to further another aspect of the present invention includes the independent-type first drug packaging apparatus and the numbering device for the drug packaging apparatus, and the unique identification information is issued by the numbering device. Therefore, the first drug packaging apparatus can use a general (existing) drug packaging apparatus. Here, at least one of the first drug packaging apparatus and the numbering device for the drug packaging apparatus may include the information adding unit, such as a printer, for adding the unique identification information to the packaging bag and the communication unit for uploading the drug information or the like of the packaged drugs in associated with the unique identification information to the cloud server.

In the drug packaging apparatus according to further another aspect of the present invention, it is preferable that the information adding unit adds the unique identification information or a barcode indicating the unique identification information to the packaging bag, or attaches to the packaging bag, a label on which the unique identification information or the barcode indicating the unique identification information is added, or records the unique identification information on an electronic tag attached to the packaging bag.

In the drug packaging apparatus according to further another aspect of the present invention, it is preferable that the information adding unit further adds, among patient information, a drug administration time and drug information of the packaged drugs, at least the drug administration time to the packaging bag.

In the drug packaging apparatus according to further another aspect of the present invention, it is preferable that the communication unit uploads the prescription data in association with the unique identification information, to the cloud server.

A packaging bag according to further another aspect of the present invention is a packaging bag which contains drugs to be taken in one dose packaged by the drug packaging apparatus described above, and to which at least the unique identification information is added.

In the packaging bag according to further another aspect of the present invention, it is preferable that the unique identification information is a GS1 identification code.

A drug package auditing apparatus according to further another aspect of the present invention includes: the drug packaging apparatus described above; an imaging unit configured to capture an image of the packaged drugs before or after the drugs are put and packaged in the packaging bag; and a drug auditing unit configured to support a pharmacist to confirm whether the packaged drugs are drugs corresponding to the prescription data based on the image of the drugs captured by the imaging unit and the prescription data.

The pharmacist can easily confirm the details (for example, engraved marks and so on of the drug) of the packaged drugs by watching the image of the packaged drugs imaged by the imaging unit, as compared with the case of directly watching the drugs. Or, when the drug auditing unit automatically inspects the packaged drug based on the image, the pharmacist can use the audit result by the drug auditing unit so that the pharmacist can perform the audit work more efficiently with less audit errors. It is preferable that the images are taken at a plurality of positions such as the front and back of the drugs, from the viewpoint of audit.

In the drug package auditing apparatus according to further aspect of the present invention, it is preferable that when the pharmacist confirms that the drugs contained in the packaging bag are drugs corresponding to the prescription data, the communication unit uploads drug information of the packaged drugs and the image used for audit in the drug auditing unit, in association with the unique identification information, to the cloud server. Thus, it is possible to confirm the image used for the audit as well as the drug information of the packaged drugs, and ensure traceability of the drug audit.

Further another aspect of the present invention is a drug package auditing apparatus including a drug packaging apparatus and a one-dose packaged drug auditing apparatus that are provided to one or more facilities, wherein the drug packaging apparatus includes a drug packing unit configured to put and package drugs to be taken in one dose according to prescription data in a packaging bag, and the one-dose packaged drug auditing apparatus includes: a unique identification information acquiring unit configured to acquire, from a numbering unit configured to issue unique identification information for uniquely specifying packaged drugs on a package basis, the identification information for packaged drugs packaged by the one or more facilities; an information adding unit configured to add the unique identification information acquired by the unique identification information acquiring unit to the packaging bag; a communication unit configured to upload at least drug information of the packaged drugs contained in the packaging bag, in association with the unique identification information, to the cloud server configured to unitarily manage packaged drugs packaged by the one or more facilities on a package basis; an imaging unit configured to capture an image of the packaged drugs before or after the packaged drugs are put and packaged in the packaging bag by the drug packaging apparatus; and a drug auditing unit configured to support a pharmacist to confirm whether the packaged drugs are drugs corresponding to the prescription data based on the image of the drugs captured by the imaging unit and the prescription data.

According to further another aspect of the present invention, the drug package auditing apparatus can be constituted by using the drug packaging apparatus and the one-dose packaged drug auditing apparatus. In particular, as the drug packaging apparatus, a general (existing) drug packaging apparatus can be used.

In the drug package auditing apparatus according to further aspect of the present invention, it is preferable that, when the pharmacist confirms that the drugs contained in the packaging bag are drugs corresponding to the prescription data, the communication unit uploads, drug information of the packaged drugs and the image used for audit in the drug auditing unit, in association with the unique identification information, to the cloud server. Thus, it is possible to confirm the image used for the audit as well as the drug information of the packaged drugs, and ensure traceability of the drug audit.

A packaging bag according to further aspect of the present invention is packaging bag which contains drugs to be taken in one dose packaged by the drug package auditing apparatus described above and to which at least the unique identification information is added.

In the packaging bag according to the further aspect of the present invention, it is preferable that the unique identification information is a GS1 identification code.

A drug management method according to further aspect of the present invention includes: a step of putting and packaging, by a drug packing unit provided to one or more facilities, drugs to be taken in one dose according to prescription data in a packaging bag; a step of issuing, by a numbering device, unique identification information for uniquely specifying packaged drugs contained in the packaging bag, on a package basis; a step of adding, by an information adding unit, the issued unique identification information to the packaging bag; and a step of uploading, by a communication unit, at least drug information of the packaged drugs contained in the packaging bag, in association with the unique identification information, to the cloud server, wherein the cloud server unitarily manages packaged drugs packaged by the one or more facilities, on a package basis. Thus, even when the identity of the packaged drugs packaged by the one or more facility such as a pharmacy is unknown, the identity of the packaged drug can be acquired by making inquiries to the cloud server based on the unique identification information added to the packaging bag, and the traceability of the packaged drugs can be ensured.

In the drug management method according to the further aspect of the present invention, it is preferable that browsing of information is restricted depending on accessing persons including doctors, pharmacists, nurses, recipients and other users of a client terminal capable of accessing the cloud server, the client terminal including an information reading unit configured to read the unique identification information added to the packaging bag and a drug information acquiring unit configured to acquire at least the drug information of the packaged drugs contained in the packaging bag from the cloud server based on the unique identification information read by the information reading unit.

According to the present invention, even for packaged drugs which have been one-dose packaged by one or more facilities, it is possible to easily acquire the drug information of the packaged drugs and ensure traceability of the packaged drugs.

BRIEF DESCRIPTION OF THE DRAWINGS

FIG. 3 is a diagram illustrating an example of a data structure managed by a drug management DB.

FIG. 6 is a diagram illustrating a first embodiment of a packaging bag according to the present invention.

FIG. 12 is a diagram an example of a list of images created by a drug auditing unit.

DESCRIPTION OF THE EMBODIMENTS

Hereinafter, preferable embodiments of a drug management system, a drug packaging apparatus, a cloud server, a drug package auditing apparatus, a packaging bag, and a drug management method according to the present invention will be described with reference to the accompanying drawings.

<Configuration of Drug Management System>

Figure 1:
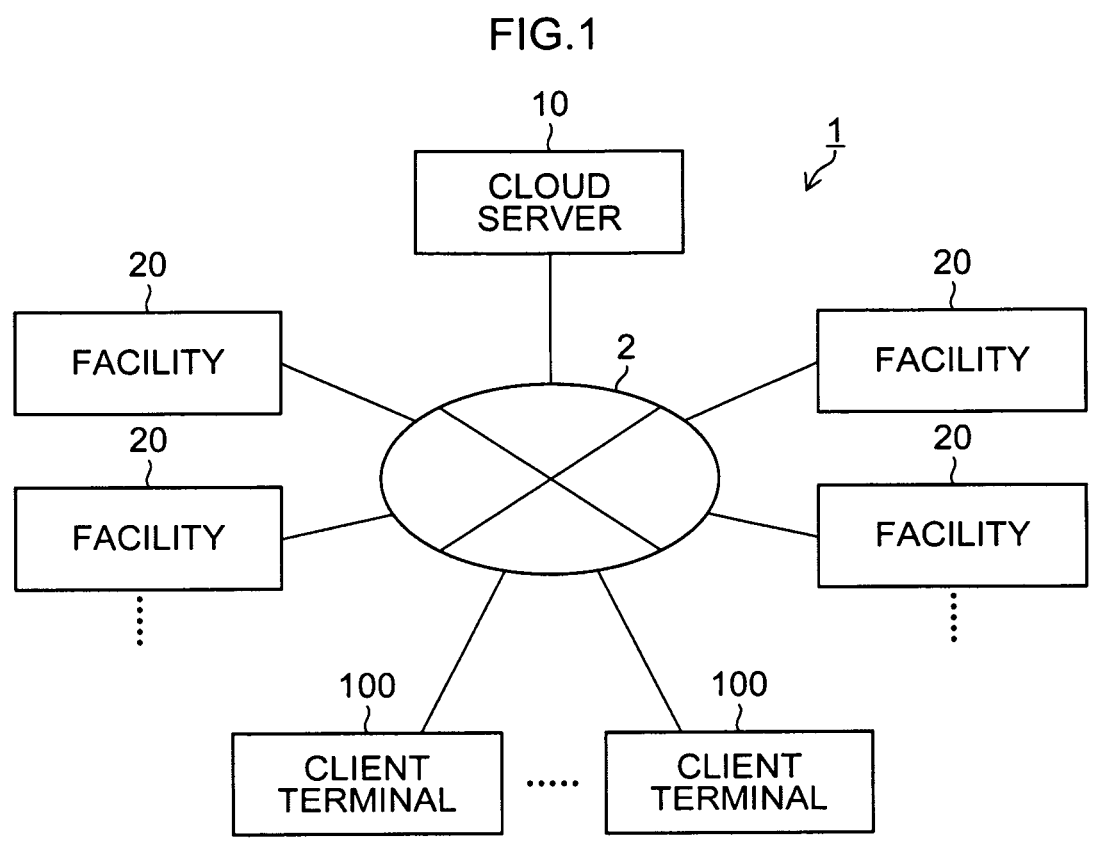
FIG. 1 is a system configuration diagram illustrating a schematic configuration of a drug management system according to the present invention.

FIG. 1 is a system configuration diagram illustrating a schematic configuration of a drug management system according to the present invention.

A drug management system 1 includes a cloud server 10, one or more facilities 20, and a client terminal 100, and is communicably connected via a network 2 such as the Internet. The network 2 is preferably a secure network suitable for medical information safety management.

<Cloud Server>

Figure 2:
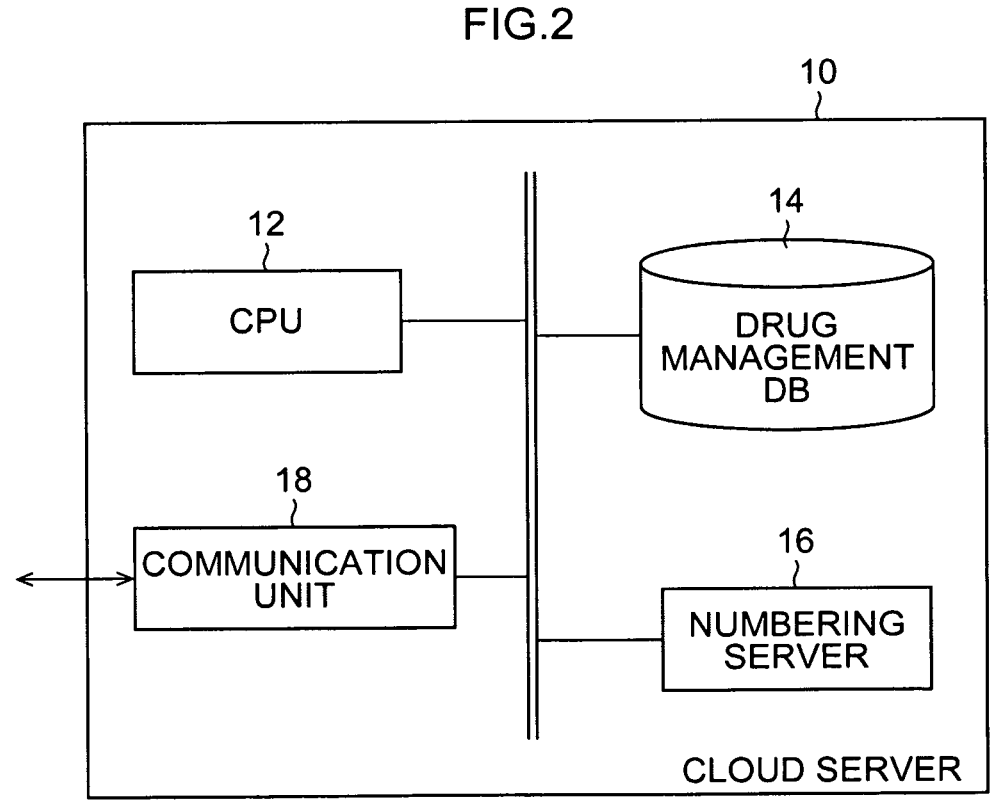
FIG. 2 is a block diagram illustrating an embodiment of a cloud server.

FIG. 2 is a block diagram illustrating an embodiment of the cloud server 10.

As illustrated in FIG. 2, the cloud server 10 is a server that unitarily manages the packaged drug bags which have been packaged by one or more facilities 20 on a package basis. The cloud server 10 mainly includes a Central Processing Unit (CPU) 12, a large capacity storage unit 14 in which drug management database (drug management DB (Database)) is stored, a numbering server 16 that functions as a numbering unit, and a communication unit 18.

The CPU 12 is a part that performs overall control of each part of the cloud server 10, and rules analysis of various information input via the communication unit 18, instructions of update and read-out of the information managed by the drug management DB, request (numbering request) to the numbering server 16 for issuance of unique identification information (unique ID (identification)) which uniquely specify the packaged drug bags on a package basis, communication processes at the communication unit 18, and the like.

FIG. 3 is a diagram illustrating an example of a data structure that is managed by the drug management DB.

As illustrated in FIG. 3, in the drug management DB, using a unique ID which is issued for each packaging bag of drugs as a primary key, drug information of packaged drug bag corresponding to the unique ID, the prescription date of the packaged drug bag, patient information, prescription hospital information, and facility information of the facility which has performed one-dose package dispensation are recorded and managed in association with each other.

The drug information of the packaged drug bag of the example includes a drug's name of each of the drugs contained in the packaged drug bag, a symbol indicating the company name (house name), and drug characters or symbol information indicating the standard, and an image (drug image) used for drug audit in a drug package auditing apparatus 22-2 (FIG. 9) which is described later. Here, the drug packaging apparatus 22-1 (FIG. 4) may include drug image information when an imaging unit is included in the dose packaging device although the drug image is not essential information as the drug information of the packaged drug bag. Furthermore, packaging information such as drug information or drug administration time and precautions may be included for each one-dose packaging bag (packaging bag).

The patient information can include the name, sex, age, etc. of the patient (recipient), and may also additionally include contact information such as the address, phone number, or the like. The hospital information can include, in addition to a name of a doctor who has prescribed the drugs, a name of a hospital where the prescribing doctor belongs. The facility information can include, in addition to a name of facility (pharmacy name when the facility is a pharmacy), a name of the pharmacist who has inspected the drug and hospital pharmacy information when the facility is a hospital pharmacy).

When receiving the request (numbering request) for issuance of unique IDs from one or more facilities 20 utilizing the system via the communication unit 18, the numbering server 16 issues the same number of unique IDs as the packaging bags of drugs (unique IDs corresponding the number of the packaging bags of drugs) and transmits the issued unique IDs to one or more facilities 20 which have sent the numbering request via the communication unit 18.

Incidentally, when the prescription data for each patient is received from one or more facilities 20 utilizing the system via the communication unit 18, the CPU 12 or the numbering server 16 interprets the prescription data, calculates the number of packaging bags of drugs corresponding to the prescription data. The numbering server 16 can issue unique IDs corresponding to the calculated number of packaging bags. In this case, the prescription data received from one or more facilities 20 correspond to the numbering request of unique IDs.

Further, when the same number of the unique IDs as the packaging bags are issued by the numbering server 16, the drug management DB illustrated in FIG. 3 can be updated based on the same number of unique IDs as the packaging bags. For example, when the prescription data for each patient is received from one or more facilities 20 via the communication unit 18, the CPU 12 can extract information managed by the drug management DB illustrated in FIG. 3 from the prescription data to update the drug management DB in association with the unique IDs.

Even when the prescription data is not received from one or more facilities 20, when the request (numbering request) for issuance of the same number of unique IDs as packaging bags is received from one or more facilities 20, the numbering server 16 can issue the same number of unique IDs as the packaging bags and transmit to the one or more facilities 20 which have sent the numbering request. Further, the CPU 12 can request the prescription data managed by the drug management DB to the one or more facilities 20 which have sent the numbering request, and cause the drug management DB to manage the prescription data in association with the same number of unique IDs as the packaging bags. At this time, the drug information to be associated with the unique IDs in the drug management DB is left blank.

Further, the unique ID issued by the numbering server 16 and uniquely specifying the packaged drug bag on a package basis is only the ID in the world. The numbering server 16 can combine the product ID uniquely specifying the drug packaging apparatus 22-1 (FIG. 4) provided to the one or more facilities 20 which have sent the numbering request, with serial numbers corresponding to the number of packaging bags to be one-dose packaged by the drug packaging apparatus 22-1 corresponding to the product ID, and issue the unique IDs, for example. Note that, when the unique IDs are issued in the manner described above, the one or more facilities 20 which send the numbering request need to notify the cloud server 10 of their product ID at the time of sending the numbering request.

Further, the numbering server 16 may issue a Universally Unique Identifier (UUID). Furthermore, the unique ID is preferably hashed by a hash value or encrypted. However, in the drug management DB, when the unique ID is not associated with personal information such as patient information and the like, it is not necessary to perform hashing or the like.

First Embodiment of One or More Facilities (Pharmacies)

Figure 4:
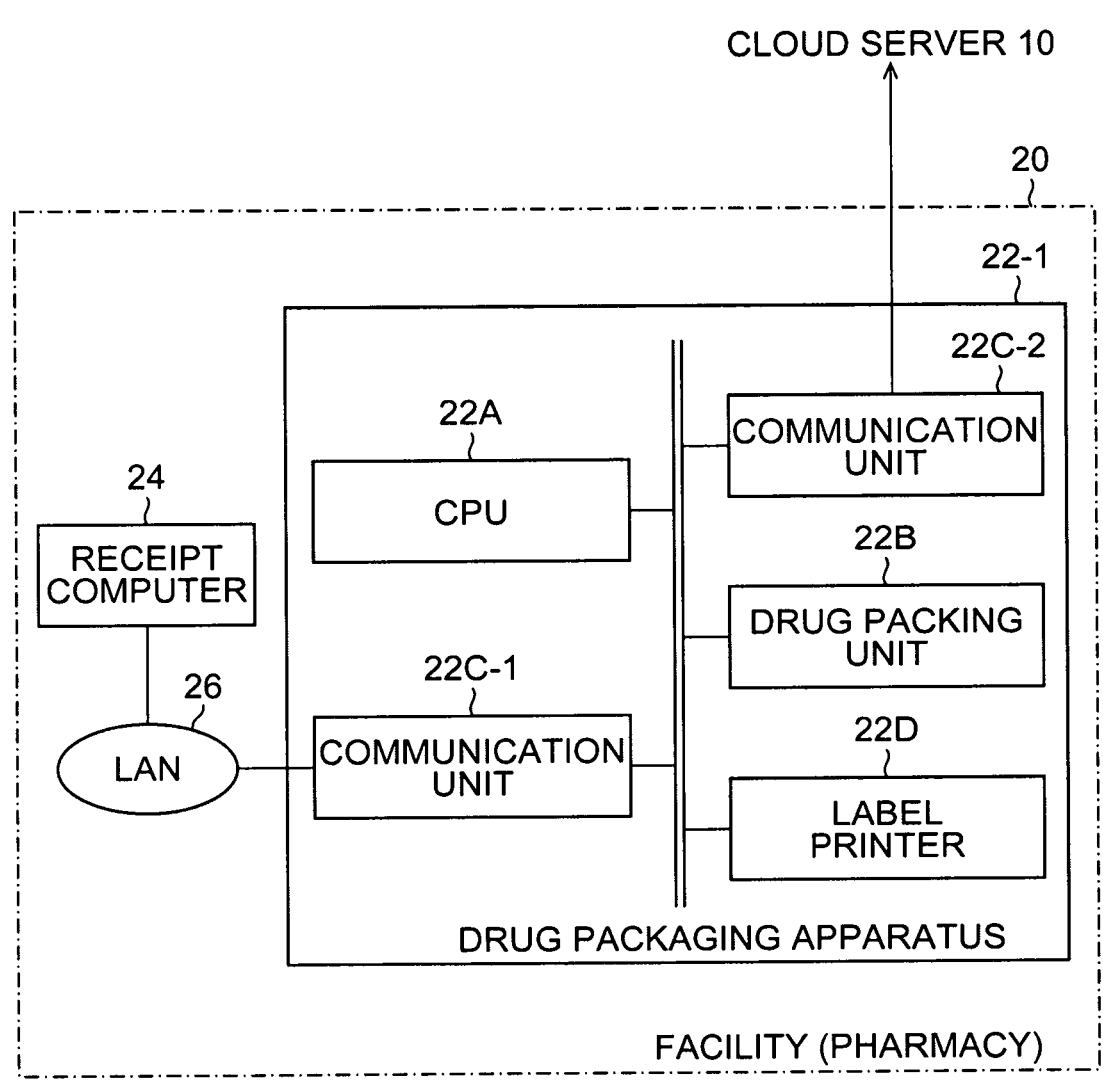
FIG. 4 is a block diagram illustrating a first embodiment of an internal configuration of a pharmacy.

FIG. 4 is a block diagram illustrating a first embodiment of an internal configuration of one or more facilities (pharmacies) 20.

As illustrated in FIG. 4, the drug packaging apparatus 22-1 and a receipt computer 24 are provided to one or more facilities (pharmacies) 20, and the drug packaging apparatus 22-1 is connected to the receipt computer 24 via a Local Area Network (LAN) 26 within one or more facilities (pharmacies) 20. Here, although one drug packaging apparatus 22-1 is provided in the example, a plurality of drug packaging apparatuses 22-1 may be provided.

The drug packaging apparatus 22-1 and the receipt computer 24 of one or more facilities (pharmacies) 20 can communicate with the cloud server 10 through a communication unit 22C-2 and the network 2 (FIG. 1).

The drug prescription work to be performed at one or more facilities (pharmacies) 20 roughly includes: a prescription data input operation by a person in charge of the pharmacy (pharmacy staff, pharmacist or the like); and dispensing work such as a picking operation by a pharmacist, a packaging operation, a drug auditing operation, and the like.

In the prescription data input operation, information described in the prescription note (hereinafter, referred to as "prescription data") is input to the receipt computer 24 by the person in charge of the pharmacy. Examples of prescription data include patient information such as patient's name and age, drug information such as a drug type of the drug or the drug's name, a dosage amount of the drug, drug usage (drug administration time) and an amount of the drug, and hospital information such as a prescription data issuing date, a prescription hospital's name and the doctor's name. Preferably, the New Standard Interface of Pharmacy-system Specifications (NSIPS (registered trademark)), which is a shared specification for a prescription interface of dispensing system, is used for the cooperation of the dispensing equipment in the pharmacy.

Next, the prescription data is output from the receipt computer 24 to the drug packaging apparatus 22-1. In addition, the pharmacist operates the receipt computer 24, or the drug packaging apparatus 22-1 which has received the prescription data to transmit the prescription data and packaging information to the cloud server 10.

In the picking operation, the pharmacist picks drugs corresponding to the drug information from the drug shelves based on the prescription data. Examples of drugs include tablets or capsules. Further, in the picking operation, for example, it is possible to use an automatic picking device that automatically picks drugs based on the prescription data received from the receipt computer.

Preferably, an audit support system automatically determines whether the picked drugs match the prescription data to prevent a picking error. Each drug is generally packaged in a Press Through Package (PTP) sheet to which drug information including dispending package unit codes (barcodes) is added. When the picked PTP sheet is placed on the stage, the audit support system reads out the drug information added to the PTP sheet. In addition, the audit support system counts the number of drugs by capturing an image of the PTP sheet, determines whether the picked PTP sheet matches the prescription data and then outputs the determination result.

The drug packaging apparatus 22-1 is a device which puts and packages a plurality of drugs to be taken in one dose in one packaging bag, to perform one-dose packaging. The drug packaging apparatus 22-1 includes a CPU 22A that performs overall control of the entire device, a drug packing unit 22B, communication units 22C-1 and 22C-2, and a label printer (printer) 22D that functions as an information adding unit.

The drug packaging apparatus 22-1 has a function to add (print) a unique ID and the like that uniquely specifies packaged drug bag on a packaging bag basis to a label using the label printer 22D and to attach the label on which the unique ID and the like are printed to the packaging bag of the drugs. Here, although the drug packaging apparatus 22-1 of the example includes a built-in type label printer 22D, the label printer 22D may be provided outside the drug packaging apparatus 22-1.

The packaging operation using the drug packaging apparatus 22-1 is carried out as follows. The pharmacist sets the drugs picked in the picking operation on the tray (drug measure) of the drug packing unit 22B, on the bag-by-bag basis (Manual Scattering Operation). The drug packing unit 22B puts the drugs of the drug measure in an empty packaging bag which is one of empty packaging bags connected in series, closes the packaging bag to package the drugs and forms perforations and the like so as to make the packaging bag separable, thereby performing one-dose packaging. Here, since the drug packaging apparatus including this type of the drug packing unit 22B is well-known, the detailed description of the configuration of the drug packing unit 22B will not be repeated.

In the drug packaging apparatus 22-1 of this example, the manual scattering operation is performed by the pharmacist. However, the drug packaging apparatus may be additionally provided with a function of automatically unpacking the drugs from the PTP sheet by setting the PTP sheet and a function of previously filling each cassette with tablets and capsules so that the manual scattering operation can be skipped. Here, drugs may be powdered.

Before the packaging operation, the CPU 22A (unique identification information acquiring unit) acquires unique IDs for the packaged drug bags with the same number as the packaging bags, which have been issued corresponding to the prescription data from the cloud server 10, via the communication unit 22C-2, and acquires the prescription data from the receipt computer 24 via the LAN 26 and the communication unit 22C-1.

The CPU 22A creates printing data for the packaged drug bags based on the acquired unique IDs and prescription data, and outputs the printing data to the label printer 22D.

The label printer 22D prints the unique IDs and the prescription data on labels by the received printing data. The printing method for the label printer 22D can be appropriately selected from thermal printing on thermal labels, printing with thermal transfer, ultraviolet (UV) ink or pigment ink on general labels, inkjet (IJ) printing with dye or pigment ink on IJ labels, and the like.

Figure 5:
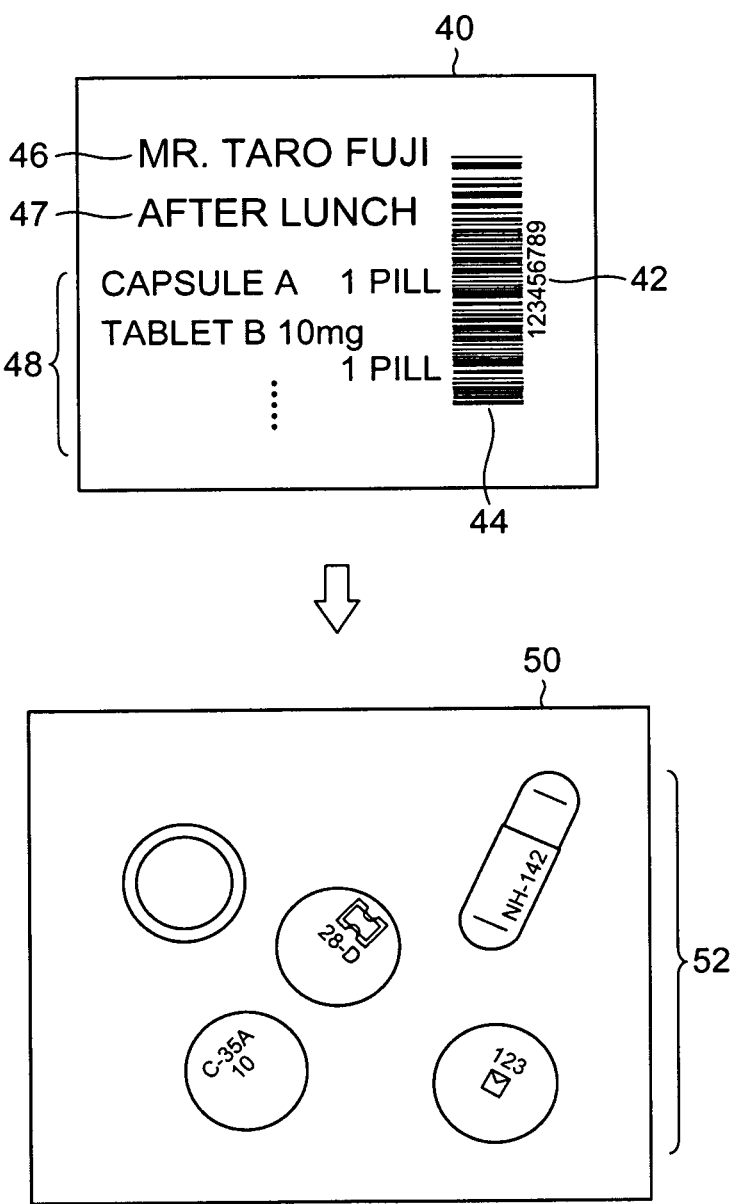
FIG. 5 is a diagram illustrating an example of a label on which a unique ID and prescription data are printed by a label printer.

FIG. 5 is a diagram illustrating an example of a label 40 on which the unique ID and the prescription data are printed by the label printer 22D.

As illustrated in FIG. 5, character information 42 of the unique ID and a barcode 44 (one-dimensional barcode) indicating the unique ID, a patient's name (Fuji Taro) 46, drug administration time (after lunch) 47, and drug character information 48 such as the drug's name of each of the packaged drugs are printed on the label 40. Here, only the character information 42 of the unique ID or the barcode 44 indicating the unique ID may be printed on the label 40. In addition, when the prescription data is printed, only the drug administration time 47 may be printed. Further, on the label 40, in addition to the barcode 44 indicating the unique ID, at least one of drug information (drug character information 48) of the packaged drugs and the patient information (patient's name 46) may be printed.

In FIG. 5, five types (four tablets and one capsule) of drugs 52 are included in the packaging bag 50 one-dose packaged by the drug packing unit 22B, and the labels 40 on which the unique IDs and the prescription data are printed by the label printer 22D are respectively attached to the corresponding packaging bags 50. Furthermore, the label printer 22D has a function of automatically attaching labels so that the label printer 22D may continuously perform the processes to acquire printing data respectively corresponding to the packaging bags 50 which are sequentially one-dose packaged by the drug packing unit 22B, from the CPU 22A, print the printing data on the labels and attach the labels to the packing bags 50.

FIG. 6 is a diagram illustrating a first embodiment of the packaging bags according to the present invention. FIG. 6 illustrates a part of a series of packaged drug bags that have been one-dose packaged and dispensed by the drug packaging apparatus 22-1. As illustrated in FIG. 6, the label 40 on which a barcode indicating the unique ID and the like is printed is attached to each of the packaging bags 50 containing the drugs.

In the drug auditing operation, the pharmacist checks, with eyes, whether types and quantities of the drugs packaged in the packaging bag 50 are correct (that is, whether the drugs are prepared according to the prescription data) to perform the drug audit.

When the drug auditing operation by the pharmacist is completed and the pharmacist inputs the audit completion, the drug packaging apparatus 22-1 uploads at least, the drug information of the packaged drugs contained in the packaging bag 50 in association with the unique ID from the communication unit 22C-2 to the cloud server 10 via the network 2. At this time, the prescription data and the packaging information may be uploaded at the same time.

Further, the drug packaging apparatus 22-1 attaches a label on which a unique ID and the like is printed by the label printer 22D to the packaging bag. However, the invention is not limited thereto. For example, instead of the label printer 22D, a thermal transfer printer or an IJ printer may be provided, and a unique ID and the like may be directly printed on the packaging bag by these printers.

In addition, the example describes the internal configuration of one or more facilities (pharmacies) 20. The internal configuration of the one or more facilities (hospital pharmacy managed by the hospital information systems HIS (Hospital Information Systems) including automatic reception management system, electronic medical record system, hospitalization management system, medical accounting system, pharmacy management system, medical appointment reservation system, and the like) 20 can be the same as the internal configuration of one or more facilities (pharmacies) 20.

First Embodiment of Drug Management Method

Figure 7:
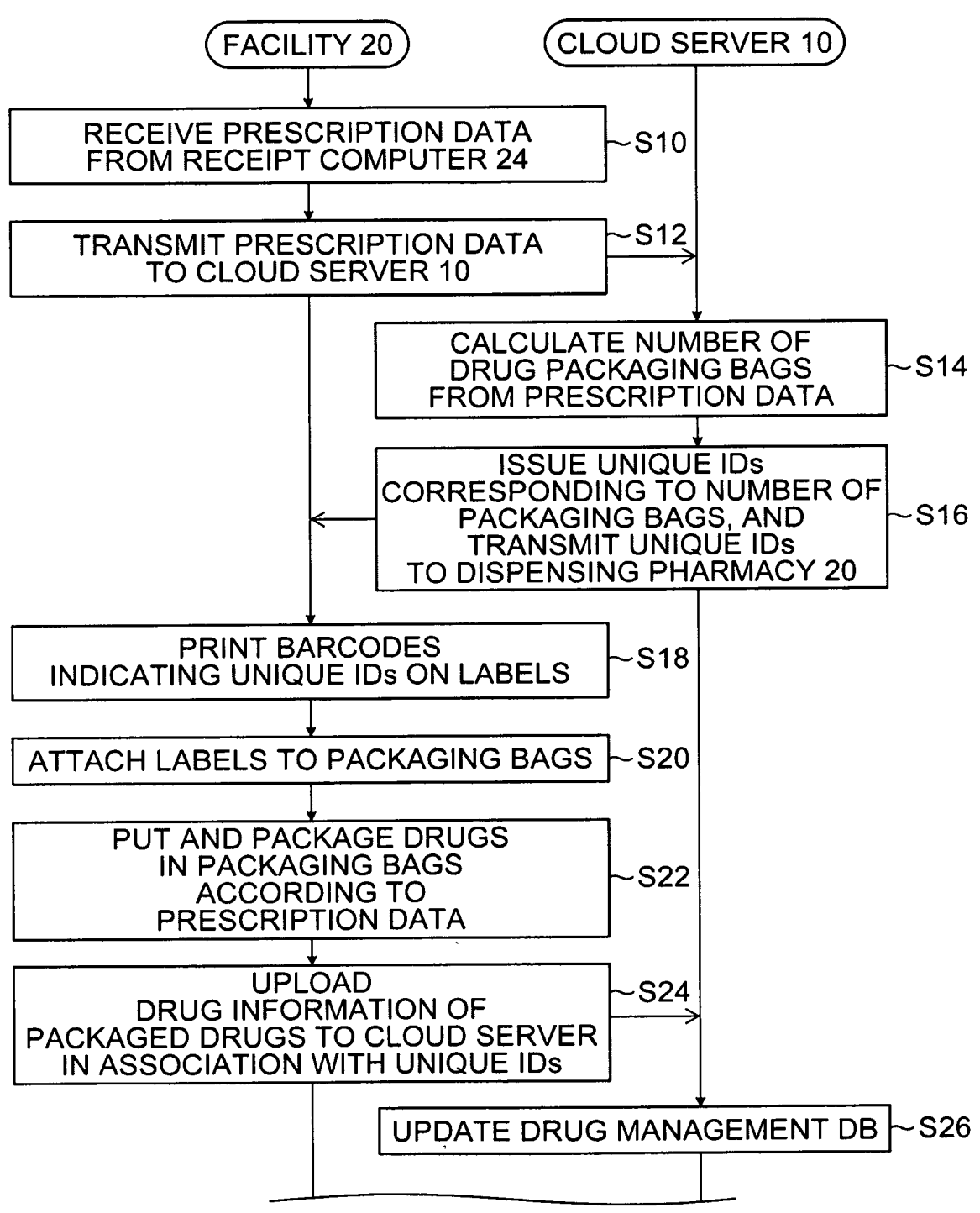
FIG. 7 is a flowchart illustrating a first embodiment of a drug management method according to the present invention.

FIG. 7 is a flowchart illustrating a first embodiment of a drug management method according to the present invention.

A drug management method according to the first embodiment illustrated in FIG. 7 is applied to the drug management system including the previously described cloud server 10 and one or more facilities (pharmacies) 20 illustrated in FIG. 6.

The drug packaging apparatus 22-1 of the one or more facilities (pharmacies) 20 receives the prescription data from the receipt computer 24 (step S10), and transmits the received prescription data to the cloud server 10 (step S12). Here, the prescription data may be transmitted from the receipt computer 24 to the cloud server 10.

The cloud server 10 calculates the number of packaging bags when the drugs are one-dose packaged, from the received prescription data (step S14). The numbering server 16 of the cloud server 10 issues the same number of unique IDs as the packaging bags, the communication unit 18 transmits the same number of unique IDs as the packaging bags, which have been issued by the numbering server 16, to the one or more facilities (pharmacies) 20 (step S16). Note that, in the example, the cloud server 10 calculates the number of packaging bags based on the prescription data received from one or more facilities (pharmacies) 20. However, the one or more facilities (pharmacies) 20 may automatically calculate or manually input the number of packaging bags of the drugs based on the prescription data, and the cloud server 10 may be requested to issue the unique IDs corresponding to the number of packaging bags calculated or input by the one or more facilities (pharmacies) 20. Preferably, the one or more facilities (pharmacies) 20 transmit to the cloud server 10, the product ID of the drug packaging apparatus 22-1 which performs one-dose packaging dispensation as information to be used in the issuance of the unique IDs by the numbering server 16.

The label printer 22D of the drug packaging apparatus 22-1 prints barcodes indicating the same number of unique IDs as the packaging bags, which have been received from the cloud server 10, drug information of the packaged drugs to be contained in the packaging bag, recipient's (patient) information and the like on labels (step S18), and attaches the printed labels on the packaging bags, respectively (step S20).

The drug packing unit 22B of the drug packaging apparatus 22-1 puts the drugs in the packaging bags according to the prescription data and forms one-dose packaging bags (step S22). Here, in the example, a label on which the unique ID and the like are printed is attached to an empty packaging bag, and then, the drugs are put in the packaging bag to be one-dose packaged. However, the label on which the unique ID and the like are printed may be attached to the packaging bag after the one-dose packaging.

When the one-dose package dispensation for one person is completed, the drug packaging apparatus 22-1 uploads the drug information of the packaged drugs and the like in association with the unique IDs, from the communication unit 22C-2 to the cloud server 10 via the network 2 (step S24).

The cloud server 10 newly registers the drug information of the packaged drugs and the like in association with the unique IDs uploaded from the one or more facilities (pharmacies) 20, on the drug management DB, and updates the drug management DB (step S26).

As a result, the cloud server 10 can unitarily manage the packaged drugs which have been one-dose packaged by the one or more facilities (pharmacies), on a packaging bag basis (bag-by-bag basis).

Second Embodiment of Drug Management Method

Figure 8:
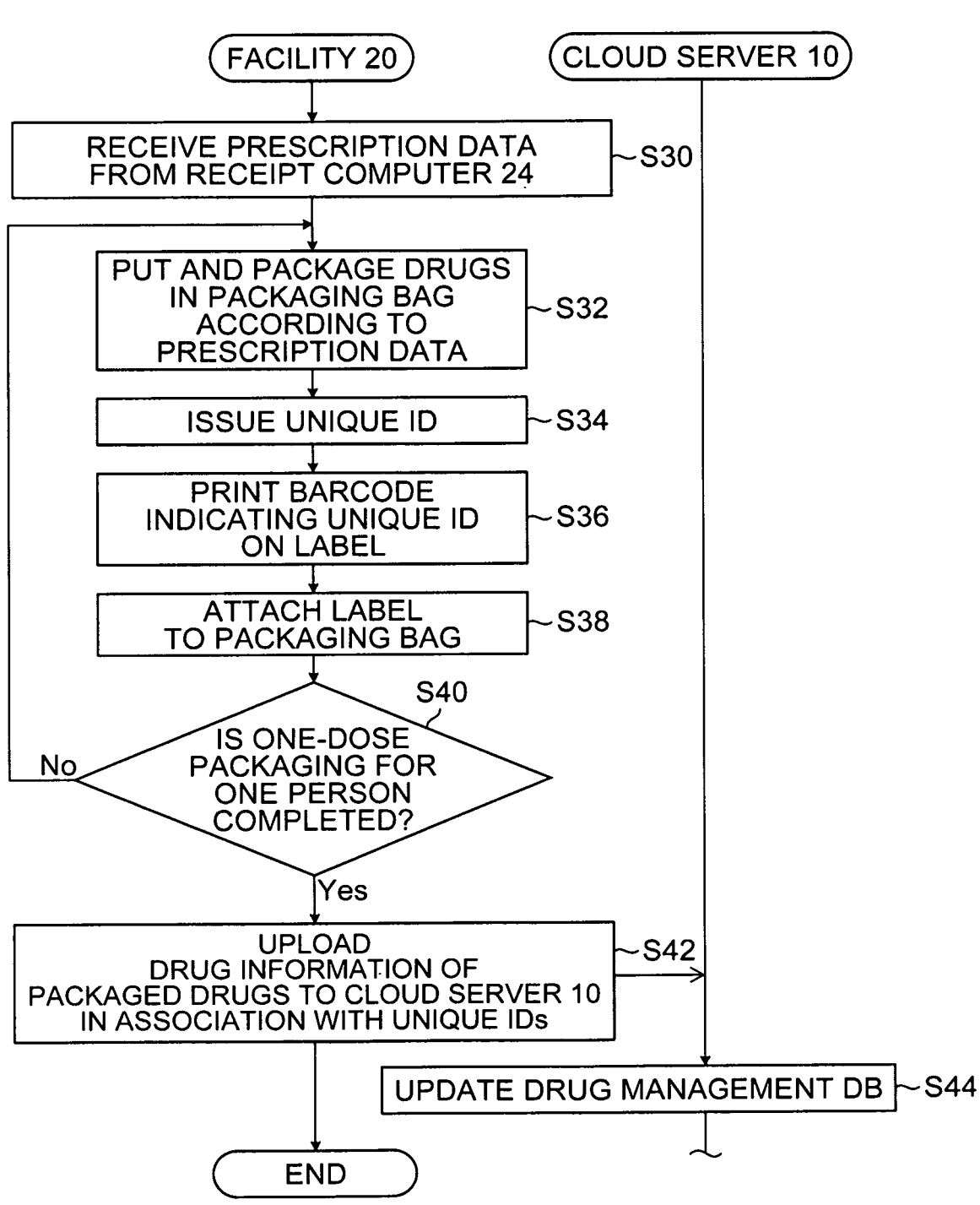
FIG. 8 is a flowchart illustrating a second embodiment of a drug management method according to the present invention.

FIG. 8 is a flowchart illustrating a second embodiment of the drug management method according to the present invention.

The drug packaging apparatus applied with the second embodiment is different from the drug packaging apparatus 22-1 illustrated in FIG. 4 in that the drug packaging apparatus includes a numbering unit and acquires unique IDs issued from the numbering unit.

In FIG. 8, the drug packaging apparatus of the one or more facilities (pharmacies) 20 receives the prescription data from the receipt computer 24 (step S30), and the drug packing unit puts and packages the drugs in the packaging bag according to the prescription data to form a one-dose packaging bag (step S32).

The numbering unit provided to the drug packaging apparatus issues a unique ID for the one-dose packaged drug bag at each time when the drugs are packaged to form a one-dose packaging bag by the drug packing unit, in the same manner as in the numbering server 16 (step S34).

The label printer provided to the drug packaging apparatus prints the issued unique ID and the like on the label (step S36), and attaches the label on which the unique ID and the like are printed to the packaging bag which has been formed (step S38).

The drug packaging apparatus determines whether the packaging for one person is completed (step S40), and when it is determined that the packaging for one person is not completed (in the case of "No"), the process returns to step S32, the processes from step S32 to step S40 are repeated. On the other hand, when it is determined that the packaging for one person is completed (in the case of "Yes"), the process proceeds to step S42.

In step S42, the drug packaging apparatus uploads the drug information of the packaged drugs and the like in association with the unique ID, to the cloud server 10 via the LAN 26 and the network 2.

The cloud server 10 newly registers the drug information of the packaged drugs associated with the unique ID uploaded from the one or more facilities (pharmacies) 20 on the drug management DB and updates the drug management DB (step S44).

As a result, the cloud server 10 can unitarily manage the packaged drugs which have been one-dose packaged by the one or more facilities (pharmacies) on a package basis.

Second Embodiment of One or More Facilities (Pharmacies) 20

Figure 9:
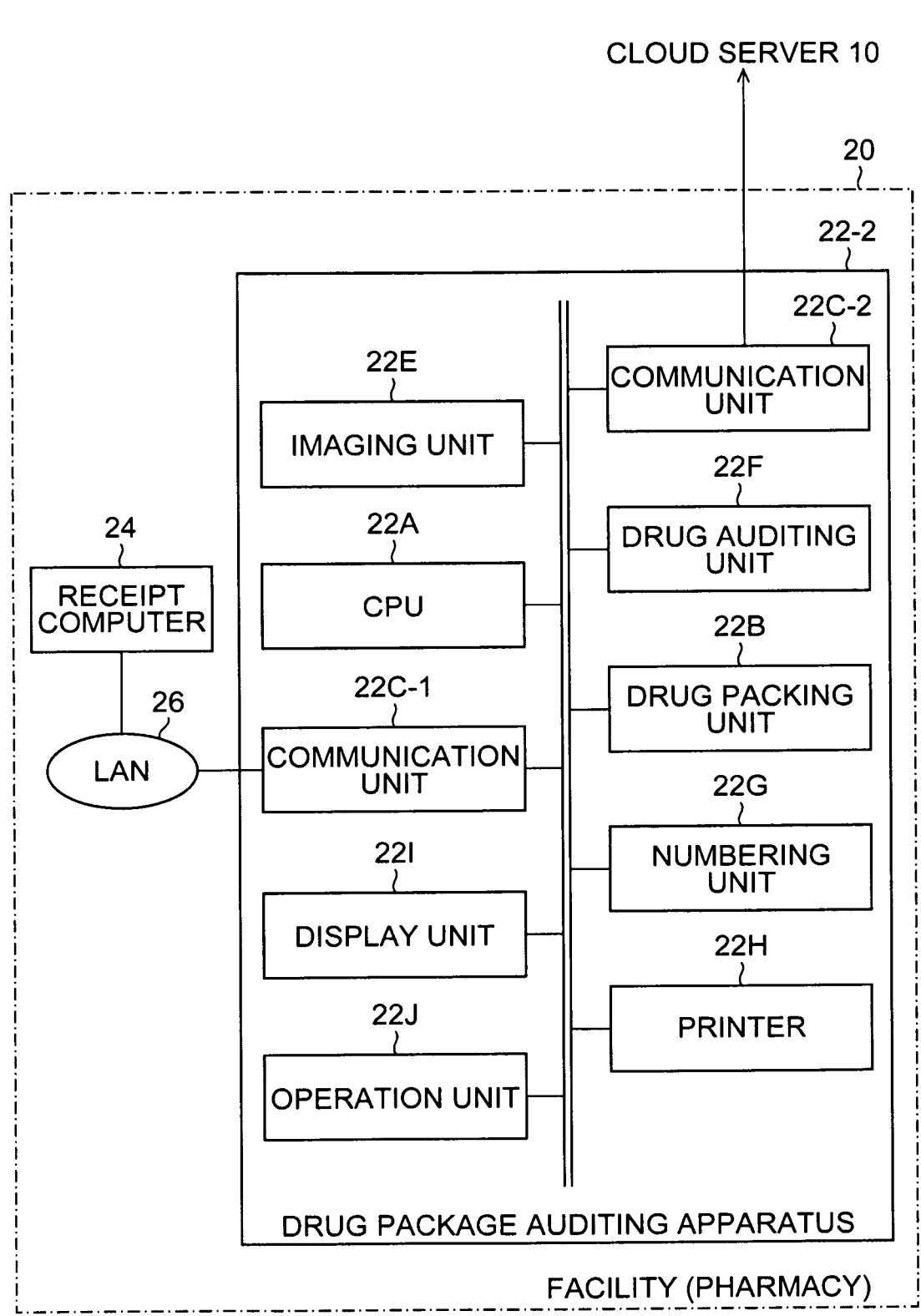
FIG. 9 is a block diagram illustrating a second embodiment of an internal configuration of a pharmacy.

FIG. 9 is a block diagram illustrating a second embodiment of the internal configuration of the one or more facilities (pharmacies) 20. Here, the components common to the internal configuration of the one or more facilities (pharmacies) 20 illustrated in FIG. 4 are given the same reference numerals, and the detailed description thereof will not be repeated.

When compared to the one or more facilities (pharmacies) 20 of the first embodiment illustrated in FIG. 4, the one or more facilities (pharmacies) 20 of the second embodiment illustrated in FIG. 9 is different in that the drug package auditing apparatus 22-2 is provided instead of the drug packaging apparatus 22-1.

The drug package auditing apparatus 22-2 illustrated in FIG. 9 mainly includes the CPU 22A that performs overall control of the entire device, the drug packing unit 22B, the communication units 22C-1 and 22C-2, an imaging unit 22E, a drug auditing unit 22F, a numbering unit 22G, a printer 22H that functions as an information adding unit, a display unit 22I, and an operation unit 22J.

The drug package auditing apparatus 22-2 is different from the drug packaging apparatus 22-1 in that the drug package auditing apparatus 22-2 includes a function of auditing packaged drugs (mainly the imaging unit 22E, the drug auditing unit 22F, etc.) and the numbering unit 22G, in addition to the packaging function similar to that of the drug packaging apparatus 22-1.

The imaging unit 22E includes a first imaging unit that images front sides of the packaged drugs (packaging bags) one-dose packaged by the drug packing unit 22B and a second imaging unit that images rear sides thereof. This configuration is to accurately grasp the shape, engraved marks and the like of the drugs. Here, the imaging unit 22E may be configured to capture an image of the drugs to be packaged before the one-dose packaging (for example, the drugs set on the tray (drug measure) of the drug packing unit 22B or the drugs dropped on the drug imaging tray from the drug measure).

When the prescription data is received from the receipt computer 24 via the LAN 26 and the communication unit 22C-1, the drug auditing unit 22F receives the images of the packaged drugs captured by the imaging unit 22E (in this example, the image captured from the front side of the one-dose packaged drugs (packaging bag) and the image captured from the rear side thereof), and determines whether the packaged drugs contained in each packaging bag are correct, based on the received prescription data and the images of the packaged drugs.

For example, such a method may be a method of determining whether the packaged drugs are correct by collating the prescription data and the information acquired by the image analysis of the images of the packaged drugs (the drug information acquired from the number of the drugs, shapes, dimensions, colors, and engraved marks of the drugs in the packaging bag, etc.), or a method of determining whether the packaged drugs are correct by acquiring the master images of the drugs in the packaging bag and comparing the master images and the captured images of the packaged drugs on a drug-by-drug basis. As the master image, it can be considered to use an image prepared in advance according to the drug information, or to use an image acquired by imaging the first package of the packaging bags.

In addition, the drug auditing unit 22F includes a function of generating an audit image for facilitating the audit of the packaged drugs by the pharmacist. The drug auditing unit 22F causes the display unit 22I to display the audit result or to display the audit image. Further, the details of the audit image will be described below.

The numbering unit 22G issues a unique ID uniquely specifying the packaged drugs on a package basis in response to the numbering request from the CPU 22A or the drug packing unit 22B. Here, the numbering request can be made on a package basis according to the packaging timing in the drug packing unit 22B or the printing timing in the printer 22H.

The unique ID issued by the numbering unit 22G is only the ID in the world, similar to the unique ID issued by the numbering server 16. For example, the unique ID can be acquired by combining a product ID uniquely specifying the drug package auditing apparatus 22-2 with a serial number corresponding to the number of packaging bags to be one-dose packaged by the drug package auditing apparatus 22-2, or with a time stamp. Furthermore, the numbering unit 22G may issue a UUID.

The CPU 22A acquires the unique ID issued by the numbering unit 22G and creates printing data for each package of drugs based on the prescription data acquired from the receipt computer 24, and then outputs the printing data to the printer 22H.

The printer 22H prints the unique ID and the prescription data on the packaging bag by the input printing data.

The display unit 22I displays the audit result performed by the drug auditing unit 22F and the audit image. The operation unit 22J functions as a user interface for inputting the audit information by the pharmacist.

When the drug auditing operation by the pharmacist is completed and the pharmacist inputs the audit completion through the operation unit 22J, the drug package auditing apparatus 22-2 uploads at least the drug information of the packaged drugs contained in the packaging bag in association with the unique ID from the communication unit 22C-2 to the cloud server 10 via the network 2. At this time, the prescription data and packaging information may be simultaneously uploaded.

Third Embodiment of Drug Management Method

Figure 10:
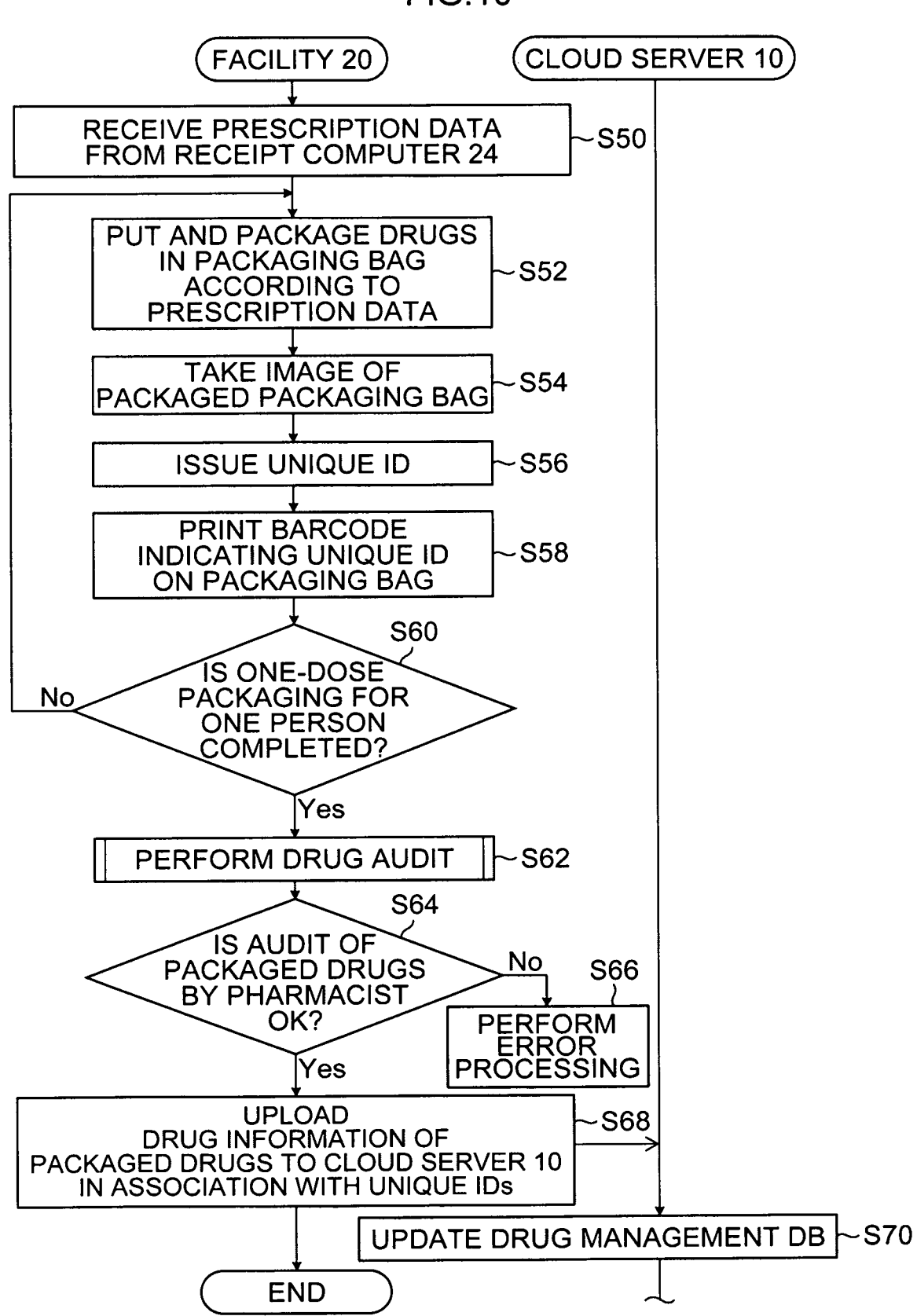
FIG. 10 is a flowchart illustrating a third embodiment of a drug management method according to the present invention.

FIG. 10 is a flowchart illustrating a third embodiment of the drug management method according to the present invention.

The drug management method of the third embodiment illustrated in FIG. 10 is applied to the drug management system including the cloud server 10 and the one or more facilities (pharmacies) 20 illustrated in FIG. 9.

In the FIG. 10, the drug package auditing apparatus 22-2 of the one or more facilities (pharmacies) 20 receives the prescription data from the receipt computer 24 (step S50), and the drug packing unit 22B puts and packages the drugs in the packaging bag according to the prescription data to form the one-dose packaging bag (step S52).

The imaging unit 22E captures an image of the packaging bag which has been one-dose packaged by the drug packing unit 22B, and outputs the image of the packaged drugs to the drug auditing unit 22F (step S54).

Further, the numbering unit 22G issues the unique ID for the one-dose packaged drugs (packaging bags) at each time when the drugs are one-dose packaged by the drug packing unit 22B (step S56). The printer 22H prints the issued unique ID and the like on the packaging bag (step S58).

The drug package auditing apparatus 22-2 determines whether the packaging for one person is completed (step S60). When it is determined that the packaging for one person is not completed (in the case of "No"), process returns to step S52, the processes from step S52 to step S60 are repeated. On the other hand, when it is determined that the packaging for one person is completed (in the case of "Yes"), the process proceeds to step S62.

Figure 11:
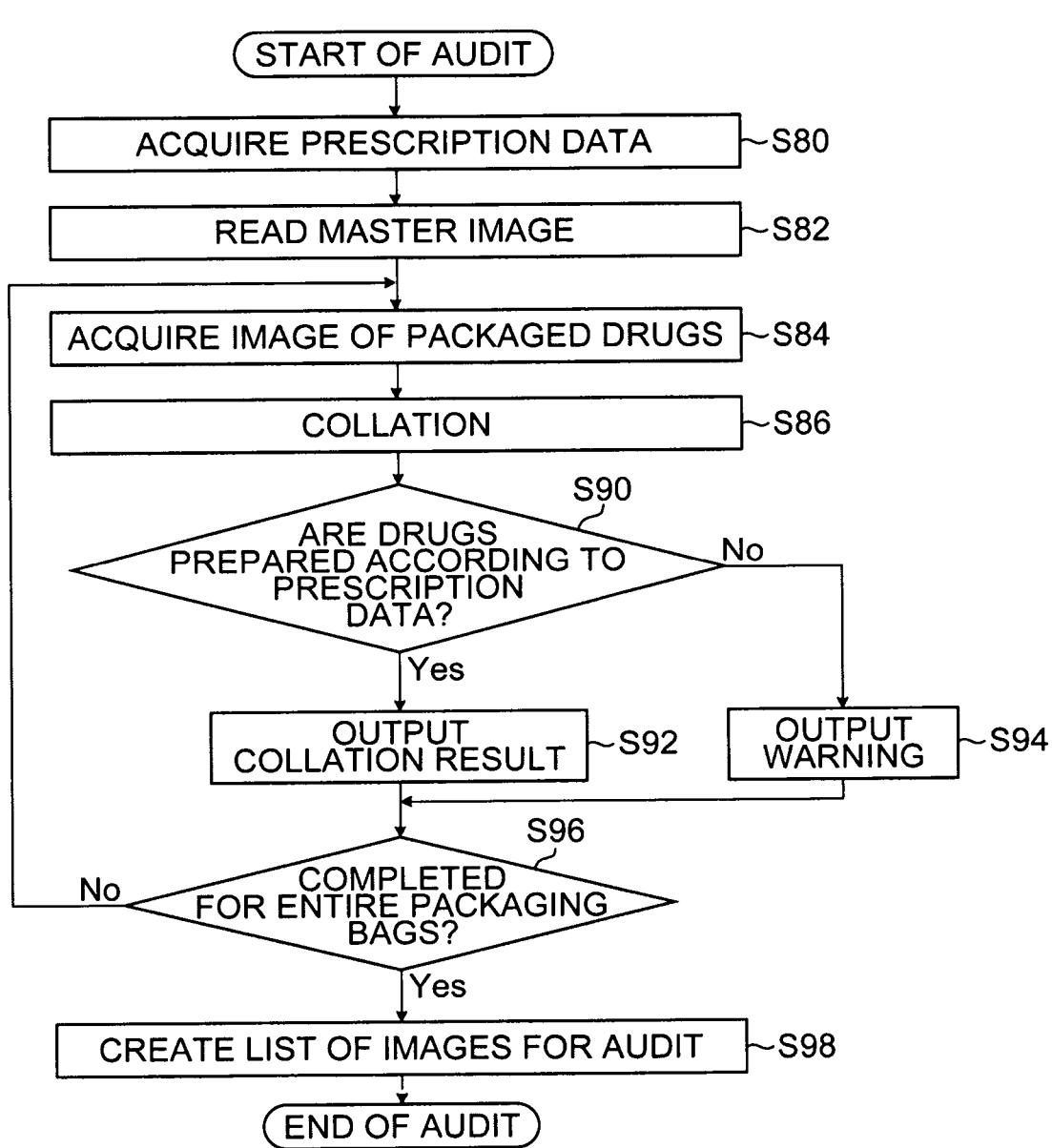
FIG. 11 is a flowchart illustrating an example of drug audit in step S62 illustrated in FIG. 10.

In step S62, the drug auditing unit 22F performs the audit. FIG. 11 is a flowchart (sub-routine) illustrating an example of the drug audit in step S62.

In FIG. 11, the drug auditing unit 22F acquires the prescription data and the packaging information from the CPU 22A (step S80), and reads out the master image corresponding to each of the packaged drugs from the drug master image group prepared in advance, based on the drug information included in the prescription data and the packaging information (step S82). Further, the drug auditing unit 22F acquires images of the packaged drugs captured by the imaging unit 22E (step S84).

The drug auditing unit 22F collates the master images and the images of the packaged drugs on a one-by-one basis (step S86). For example, a feature quantity of each drug is extracted from the image to be collated (collation-target image) and a feature quantity of each drug is also extracted from the master image, and then, the extracted feature quantities are compared, thereby performing collation of the name and quantity of each of the packaged drugs. As the feature quantity, the shape, size, color, engraved marks, characters, or the like can be exemplified. Further, local feature quantities such as Scale-Invariant Feature Transform (SIFT) may be extracted and used in the collation.

As a result of the collation in step S86, when the packaged drugs are in accordance with the prescription data and the packaging information (Yes in step S90), the process proceeds to step S92 and the collation result (for example, "the second packaging bag is packaged in accordance with the prescription data and the packaging information") is output to the display unit 22I. When the packaged drugs are not in accordance with the prescription data and the packaging information (No in step S90), the process proceeds to step S94 (warning process) and a warning is output. As the warning output (display on the display unit 22I) in step S94, for example, a message of "the packaged drugs in the second packaging bag are different from the contents of the prescription data or the packaging information" and a message indicating detailed contents of the warning ("Unnecessary drug C is put instead of drug B in the packaging bag") can be output to the display unit 22I.

When a collation result (step S92) or a warning (step S94) is output, the drug auditing unit 22F determines whether the collation for the entire packaging bags of one patient is completed (step S96). When the determination is negative (No in step S96), the process returns to step S84, and the processes from step S84 to step 96 are performed for the next packaging bag. When the determination is affirmative (Yes in step S96), the process proceeds to step S98.

In step S98, the drug auditing unit 22F creates a list of audit images which facilitates audit by the pharmacist for the packaged drugs which have been one-dose packaged, and displays the created the list on the display unit 22I. It is preferable that the list indicates the name and image of the drug master for packaged drugs, the name of the audit-target drugs, and captured images of the front surface and rear surface of the drugs, in terms of easiness in distinction.

FIG. 12 is a diagram illustrating an example of an audit image list created by the drug auditing unit 22F.

In the audit image list illustrated in FIG. 12, the column corresponds to each drug and the row corresponds to each packaging bag. For example, it is assumed that five types of drugs from "drug 1" to "drug 5" are prescribed in prescription data. In addition, the drug is prescribed for 10 days and the time of taking the drug is assumed to be three times: morning, noon, and night. In this case, the prescribed drugs are packaged in packaging bags of 3×10=30 bags, and the number of packaging bags of audit targets is 30.

The names of drugs corresponding to the respective columns ("drug 1", "drug 2", . . . "drug 5") are arranged in the uppermost row of the list, and master images of the respective drugs are arranged in the next row. For example, according to the respective audit results for the 30 packaging bags, the drug auditing unit 22F arranges a drug region image (audit image) which has been determined to match a master image, in a column for each drug of the master image. For example, an image determined as "drug 1" is arranged in a column for "drug 1", and an image determined as "drug 2" is arranged in a column for "drug 2".

Although not illustrated in FIG. 12, the list may include a check box by the pharmacist. In addition, the list may include a box for displaying the audit result (collation result, warning) by the drug auditing unit 22F.

The drug package auditing apparatus 22-2 preferably stores the audit result including the list of the audit image in association with the prescription data in a storage unit (not illustrated).

Returning to FIG. 10, after the drug audit in step S62 is performed, the pharmacist visually checks the list (see FIG. 12) of the audit images displayed on the display unit 22I, and determines whether the drugs are packaged in each of the packaging bags according to prescription data and packaging information (step S64). In addition, the pharmacist compares the images in the columns corresponding to each packaged drug with each other in the list of the audit images displayed on the display unit 22I. Thus, the pharmacist can easily check whether the drugs are packaged in each of the packaging bags according to the prescription data and the packaging information, and examine carefully the packaging bags for which warning has been issued in particular.

In step S64, when the packaging bag (inaccurate packaging bag), which has not been packaged according to the prescription data and the packaging information, is found (in the case of "No"), an error process is performed (step S66). As an error process, the pharmacist separates the inaccurate packaging bag from a series of packaging bags and replaces it with an appropriate packaging bag which is newly packaged. In this case, the appropriate packaging bag may be printed with a barcode or the like the same as the ones printed on the inaccurate packaging bag, or may be printed with a barcode or the like indicating a newly issued unique ID.

In step S64, when the pharmacist confirms that all the packaging bags are packaged according to the prescription data and the packaging information (in the case of "Yes"), based on the instruction input on the operation unit 22J by the pharmacist, the drug package auditing apparatus 22-2 uploads drug information of the packaged drugs contained in the packaging bags in association with the unique IDs from the communication unit 22C-2 to the cloud server 10 via the network 2 (step S68).

As drug information, as illustrated in FIG. 3, it is preferable to upload drug images (two images acquired by imaging the packaging bag from the front and back and/or images of packaged drugs) in addition to drug character information. Moreover, the prescription data and the packaging information may be uploaded at the same time. Furthermore, when the drug image is uploaded to the cloud server 10, the drug image may be resized or compressed.

The cloud server 10 newly registers drug information or the like of the packaged drugs associated with the unique IDs uploaded from the one or more facilities (pharmacies) 20, in the drug management DB, and updates the drug management DB (step S70).

Thus, the cloud server 10 can unitarily manage the packaged drugs which have been one-dose packaged by the one or more facilities, in a package basis (package-by-package basis).

Third Embodiment of One or More Facilities (Pharmacies) 20

Figure 13:
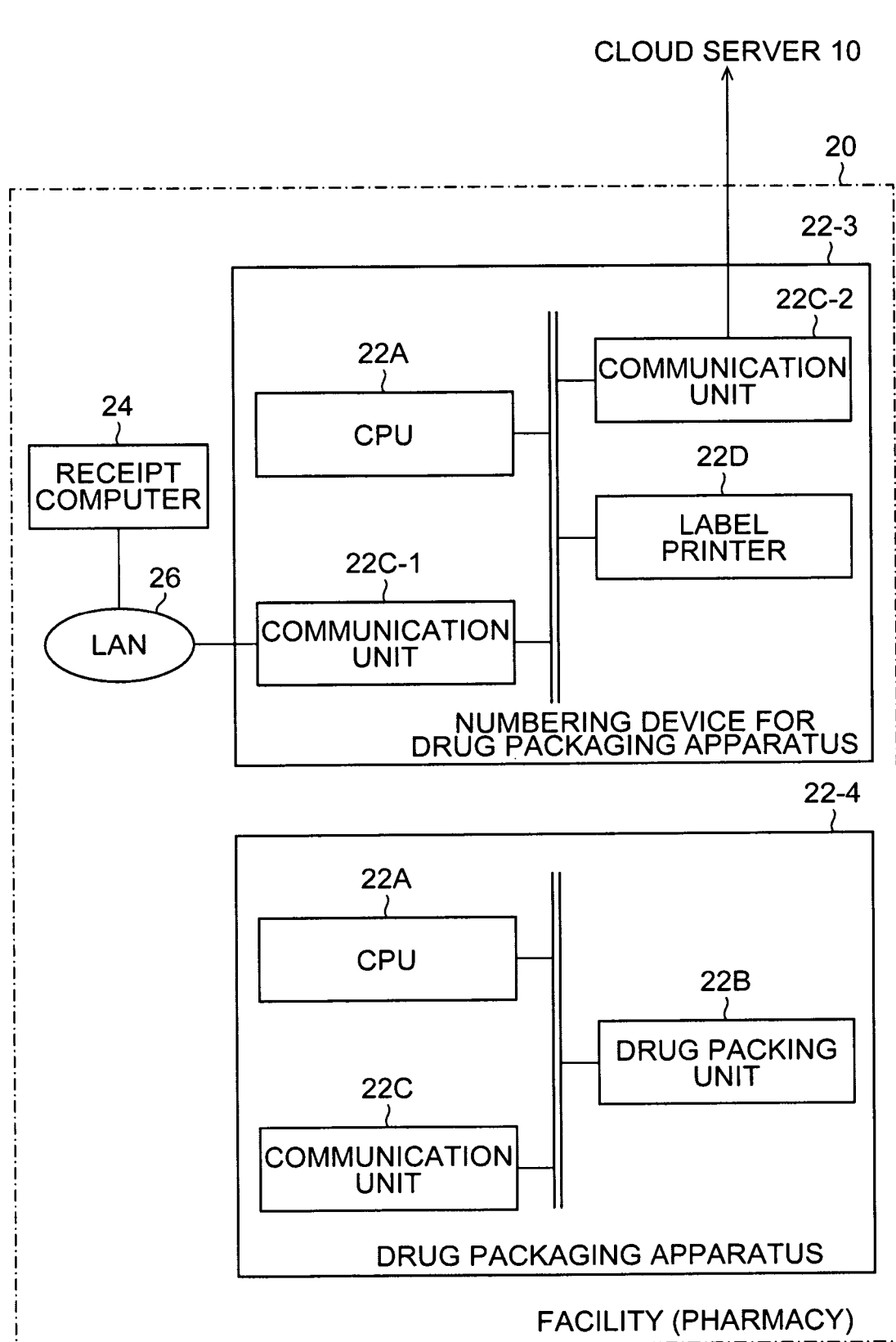
FIG. 13 is a block diagram illustrating a third embodiment of an internal configuration of a pharmacy.

FIG. 13 is a block diagram illustrating a third embodiment of an internal configuration of the one or more facilities (pharmacies) 20. The parts common for the first embodiment illustrated in FIG. 4 are denoted by the same reference numerals, and detailed description will not be repeated.

In the one or more facilities (pharmacies) 20 illustrated in FIG. 13, a numbering device (numbering device) 22-3 for the drug packaging apparatus and a drug packaging apparatus 22-4 are provided independently. The numbering device 22-3, the drug packaging apparatus 22-4, and a receipt computer 24 can communicate with each other via a LAN 26.

Each time when the drugs are one-dose packaged by a drug packing unit 22B of the drug packaging apparatus 22-4, the numbering device 22-3 issues the unique ID for the one-dose packaged drugs in the same manner as the numbering server 16.

The unique ID issued by the numbering device 22-3 is only the ID in the world, and includes a GS1 identification code which is an international standard defined by GS1 (General Specifications One), for example.

Examples of the GS1 identification codes include a GTIN (Global Trade Item Number) code, a GLN (Global Location Number) code, a GIAI (Global Individual Asset Identifier) code, an SSCC (Serial Shipping Container Code), a GRAI (Global Returnable Asset Identifier) code, a GSRN (Global Service Relation Number) code, a GDTI (Global Document Type Identifier) code, and a GCN (Global Coupon Number) code, and preferably include the GSRN code and the GIAI code in particular.

The GSRN code is an identification code for managing a service provider and a user of a service. The GSRN code consists of: in addition to a 9-digit GS1 business entity code and 8-digit service provider/user codes, a combination of a 10-digit extension area and 15-digit unique code that can be defined arbitrarily. Therefore, for example, a product ID (serial number) of the drug packaging apparatus or the drug package auditing apparatus may be assigned to the service provider/user code of the GSRN code. A serial number corresponding to the number of packaging bags to be one-dose packaged by the drug packaging apparatus or the drug package auditing apparatus having the product ID, or a time stamp, may be assigned to the extension area or the unique code. Thereby, the GSRN code can be a unique ID for uniquely specifying the packaged drugs on a package basis.

In addition, the GIAI code is an identification code for managing company assets, and is a maximum 30-digit code including a 9-digit GS1 business entity code and a 1 to 21-digit asset number having a variable-length. Accordingly, a product ID of the drug packaging apparatus or the drug package auditing apparatus and a serial number corresponding to the number of packaging bags to be one-dose packaged by the drug packaging apparatus or the drug package auditing apparatus having the product ID, or a time stamp, can be assigned to the 21-digit asset number of the GIAI code. Thereby, the GIAI code can be a unique ID for uniquely specifying the packaged drugs on a package basis.

A CPU 22A-1 creates print data for each packaging bag of drugs based on the issued unique ID and the prescription data acquired from the receipt computer 24, and outputs the created print data to a label printer 22D.

The label printer 22D prints the unique ID and the prescription data using the input print data. The printed label is automatically or manually added to the packaging bag which is one-dose packaged by the drug packing unit 22B of the drug packaging apparatus 22-4. Further, the label printer 22D may be a normal printer (an IJ printer, an electronic photograph, or the like), and may print a list of unique IDs and various types of prescription data corresponding to the packaging bags which have been one-dose packaged, on normal paper to provide the list and the one-dose packaged drugs as a set.

The drug packaging apparatus 22-4 includes a CPU 22A, a drug packing unit 22B, and a communication unit 22C. The drug packaging apparatus 22-4 performs one-dose packaging of drugs by mainly putting the drugs in the drug measure, which have been set for each one-dose package in the drug measure, in a series of empty packaging bags, closing the packaging bags, and making it possible to separate by applying perforation. As such a drug packaging apparatus 22-4, a general device (an existing device) can be applied.

According to the third embodiment, the numbering device 22-3 for the drug packaging apparatus is provided, and the numbering device 22-3 can communicate with the general drug packaging apparatus 22-4 via a communication line such as the LAN 26. Thus, the configuration which is equivalent to the drug packaging apparatus 22-1 illustrated in FIG. 4 can be achieved.

In this example, the label printer 22D (printer) and the communication unit 22C-2, which can communicate with the cloud server 10, are provided on the side of the numbering device 22-3 for the drug packaging apparatus. However, they may be provided on the side of the drug packaging apparatus 22-4.

Figure 14:
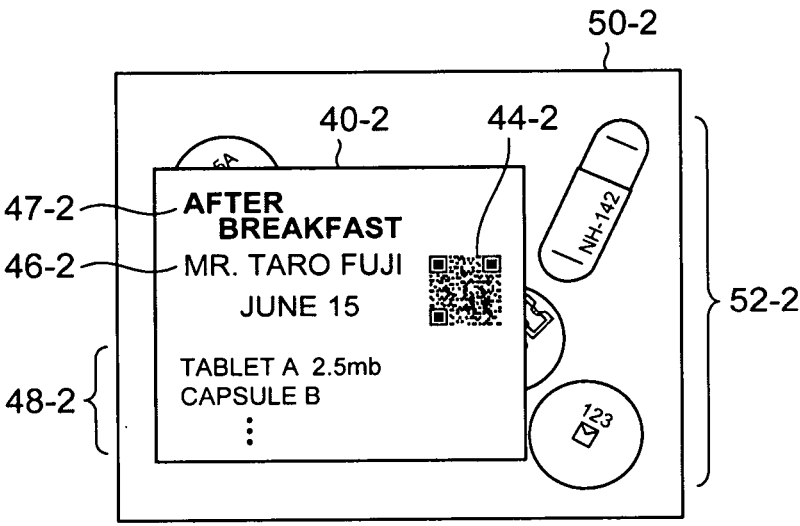
FIG. 14 is a diagram illustrating a second embodiment of a packaging bag according to the present invention.

In addition, FIG. 14 is a diagram illustrating a second embodiment of the packaging bag according to the present invention. FIG. 14 is a plane view of a packaging bag for one-dose packaging which contains drugs to be taken at a time (in one dose).

A packaging bag 50-2 illustrated in FIG. 14 is configured such that a plurality of drugs 52-2 to be taken in one dose are contained in the drug packing unit 22B, a label 40-2 is attached, and a unique ID and prescription data are printed on the label 40-2 by the label printer 22D.

The label 40-2 is printed with a two-dimensional barcode 44-2 (for example, QR code (registered trademark)) indicating a unique ID (a unique ID including a GSRN code which is one of GS1 identification codes in this example), a patient's name (Taro Fuji) 46-2, a drug administration time (after breakfast) 47-2, and drug character information 48-2 such as a drug's name for each of the one-dose packaged drugs. When prescription data is printed, only the drug administration time 47-2 may be printed. Further, the label 40-2 may be printed with at least one of drug information (drug character information 48-2) of the packaged drugs and patient information (patient's name 46-2) in addition to the two-dimensional barcode 44-2 indicating the unique ID.

Fourth Embodiment of One or More Facilities (Pharmacies) 20

Figure 15:
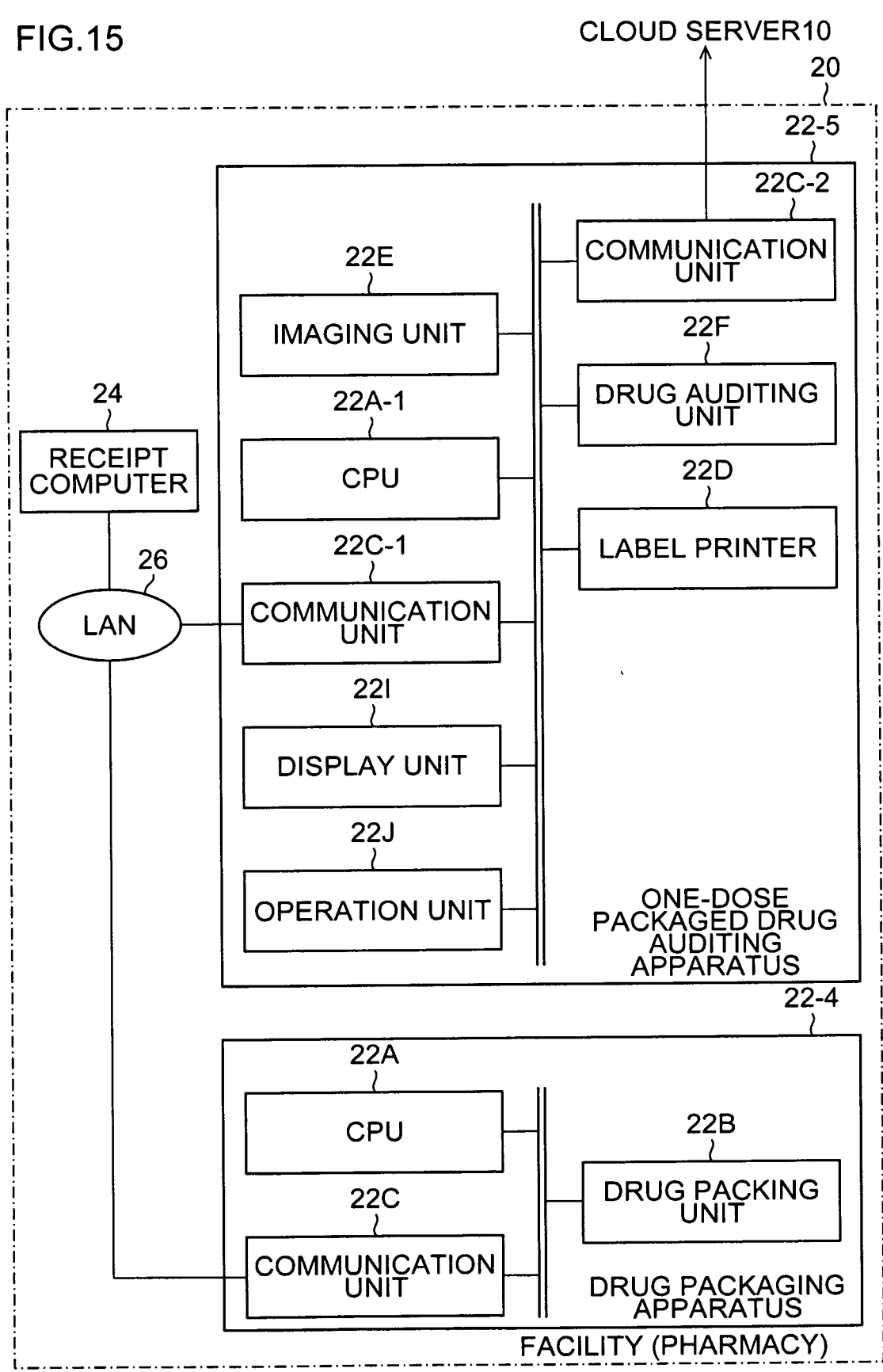
FIG. 15 is a block diagram illustrating a fourth embodiment of an internal configuration of a pharmacy.

FIG. 15 is a block diagram illustrating a fourth embodiment of an internal configuration of the one or more facilities (pharmacies) 20. The parts common for the first embodiment illustrated in FIG. 4 and the second embodiment illustrated in FIG. 9 are denoted by the same reference numerals, and detailed description will not be repeated.

In the one or more facilities (pharmacies) 20 illustrated in FIG. 15, a drug packaging apparatus 22-4 and a one-dose packaged drug auditing apparatus 22-5 are provided independently, and the drug packaging apparatus 22-4, the one-dose packaged drug auditing apparatus 22-5, and a receipt computer 24 can communicate with each other via a LAN 26.

The drug packaging apparatus 22-4 has a packaging function similar to that of the drug packaging apparatus 22-1 illustrated in FIG. 4. The one-dose packaged drug auditing apparatus 22-5 is comprehensively controlled by a CPU 22A-1 and has an auditing function of packaged drugs which have been one-dose packaged. The drug packaging apparatus 22-4 and the one-dose packaged drug auditing apparatus 22-5 function as a drug package auditing apparatus equivalent to the drug package auditing apparatus 22-2 of FIG. 9 according to the second embodiment.

As the drug packaging apparatus 22-4, a general device (an existing device) can be applied.

According to the fourth embodiment, the one-dose packaged drug auditing apparatus 22-5 is provided, and the one-dose packaged drug auditing apparatus 22-5 can communicate with the general drug packaging apparatus 22-4 via a communication line such as the LAN 26. Therefore, the configuration which is equivalent to the drug package auditing apparatus 22-2 illustrated in FIG. 9 can be achieved.

<Client Terminal>

Figure 16:
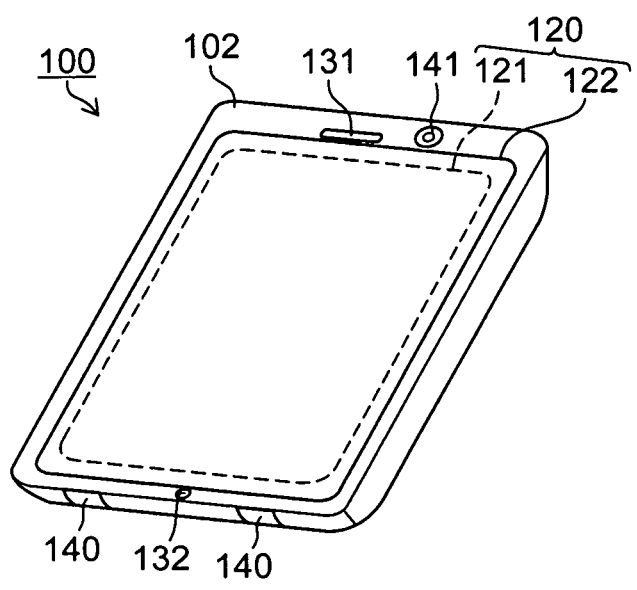
FIG. 16 is an external view of a client terminal applicable to the drug management system.

FIG. 16 is an external view of a client terminal 100 applicable to the drug management system 1, and a smartphone is used as the client terminal 100 in this example.

<<Configuration of Client Terminal>>

The client terminal 100 illustrated in FIG. 16 includes a flat housing 102. On one surface of the housing 102, a display input unit 120 is provided. In the display input unit

120, a display panel 121 serving as a display unit and an operation panel 122 serving as an input unit are integrally formed. In addition, the housing 102 includes a speaker 131, a microphone 132, an operation unit 140, and a camera unit 141 (imaging unit). Note that, the configuration of the housing 102 is not limited thereto. The housing 120 may have, for example, a configuration in which a display unit and an input unit are provided independently, or a configuration having a folding structure or a sliding mechanism. Further, as the client terminal 100, a robot including a communication mechanism via a communication means such as Wi-Fi or Bluetooth can be employed.

Figure 17:
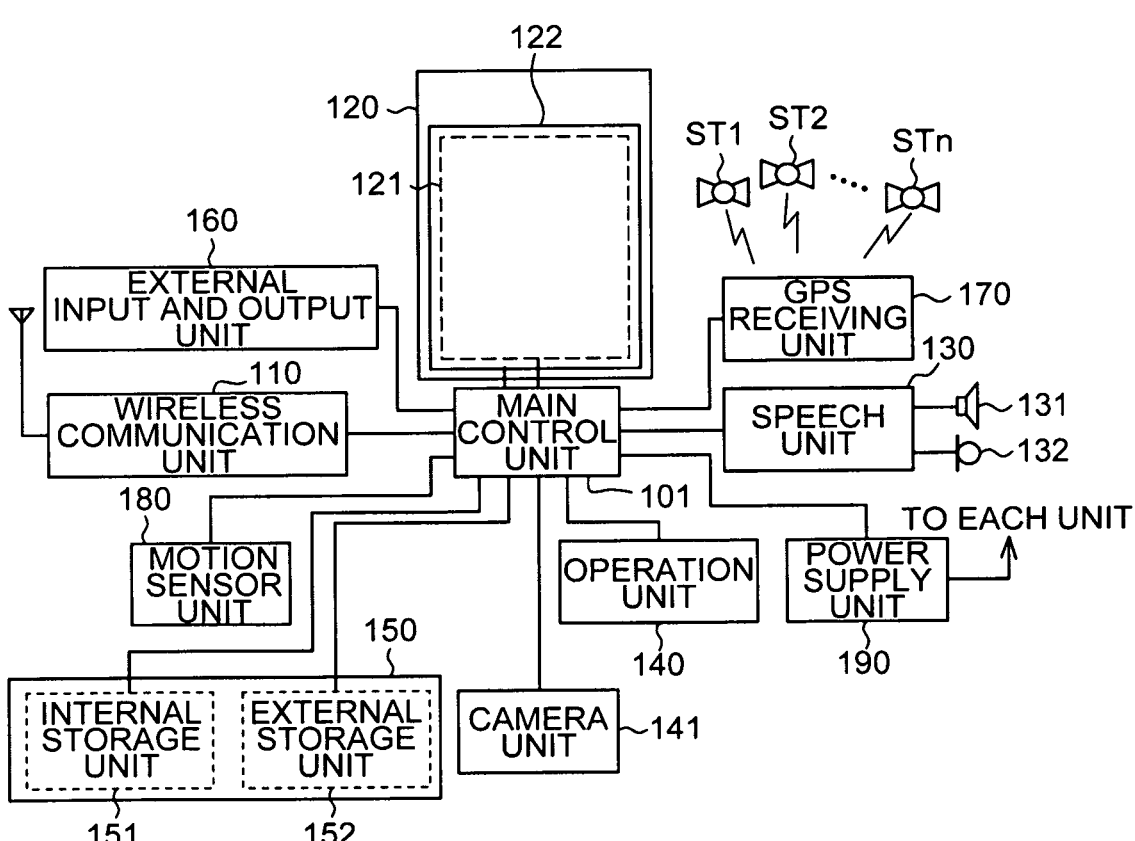
FIG. 17 is a block diagram an internal configuration of the client terminal illustrated in FIG. 16.

FIG. 17 is a block diagram illustrating an internal configuration of the client terminal 100 illustrated in FIG. 16.

As illustrated in FIG. 17, main components of the client terminal 100 include a wireless communication unit 110, a display input unit 120, a calling unit 130, an operation unit 140, a camera unit 141, a storage unit 150, an external input and output unit 160 (output unit), a global positioning system (GPS) receiving unit 170, a motion sensor unit 180, a power supply unit 190, and a main control unit 101. Further, a main function of the client terminal 100 includes a wireless communication function of performing mobile wireless communication with a base station device via a mobile communication network.

The wireless communication unit 110 performs wireless communication with the base station device contained in the mobile communication network according to an instruction from the main control unit 101. Using the wireless communication, transmission and reception of various types of file data such as voice data and image data, electronic mail data, or the like, or reception of Web data, streaming data, or the like is performed.

The display input unit 120 is a so-called touch panel that includes an operation panel 122 disposed on a screen of a display panel 121 and displays an image (still image and a moving image), text information, or the like to visually transfer information to a user and detects a user operation for the displayed information under control of the main control unit 101. For convenience, the operation panel 122 is also referred to as a touch panel.

The display panel 121 uses a liquid crystal display (LCD), an organic electro-luminescence display (OELD), or the like as a display device. The operation panel 122 is a device that is mounted so that an image displayed on a display surface of the display panel 121 can be viewed and detects one or a plurality of coordinates at which the device is operated by a user's finger or a stylus. In a case where such a device is operated by the user's finger or the stylus, the operation panel 122 outputs a detection signal generated due to the operation to the main control unit 101. Then, the main control unit 101 detects an operation position (coordinates) on the display panel 121 based on the received detection signal.

As illustrated in FIG. 16, the display panel 121 and the operation panel 122 of the client terminal 100 integrally forms the display input unit 120, and the operation panel 122 is arranged to completely cover the display panel 121. In a case where such an arrangement is adopted, the operation panel 122 may have a function of detecting a user operation input to a region outside the display panel 121, as well. In other words, the operation panel 122 may include: a detection region (hereinafter referred to as a display region) for an overlapping portion that overlaps the display panel 121; and a detection region (hereinafter referred to as a non-display region) for an outer edge portion other than the display region that does not overlap the display panel 121.

A size of the display region and a size of the display panel 121 may completely match each other, but do not necessarily match each other. Further, the operation panel 122 may include two sensitive regions including an outer edge portion and an inner portion other than the outer edge portion. Further, a width of the outer edge portion is designed as appropriate according to a size of the housing 102, or the like. Further, examples of a position detection scheme adopted in the operation panel 122 may include a matrix switch scheme, a resistive film scheme, a surface acoustic wave scheme, an infrared scheme, an electromagnetic induction scheme, and an electrostatic capacitive scheme, and any of the schemes can be adopted.

The calling unit 130 includes a speaker 131 or a microphone 132, and converts user voice input via the microphone 132 into voice data which can be processed by the main control unit 101 and outputs the voice data to the main control unit 101, or decodes voice data received by the wireless communication unit 110 or the external input and output unit 160 and outputs the decoded voice data from the speaker 131. Further, as illustrated in FIG. 16, for example, the speaker 131 and the microphone 132 can be mounted on the same surface as a surface on which the display input unit 120 is provided.

The operation unit 140 is a hardware key using a key switch, and receives an instruction from the user. For example, as illustrated in FIG. 16, the operation unit 140 is a push button type switch that is mounted on side surface of the housing 102 of the client terminal 100, and is switched on when pressed by a finger or the like and switched off by restoring force of a spring or the like when the finger is released.

The storage unit 150 stores a control program or control data of the main control unit 101, address data associated with a name or a telephone number of a communication partner, data of a transmitted or received electronic mail, web data downloaded by web browsing, and downloaded content data, and temporarily stores streaming data or the like.

Further, the storage unit 150 includes an internal storage unit 151 and an external storage unit 152 having a slot for a detachable external memory. Each of the internal storage unit 151 and the external storage unit 152 included in the storage unit 150 is realized using a storage medium such as a flash memory type memory, a hard disk type memory, a multimedia card micro type memory, a card type memory, a random access memory (RAM), or a read only memory (ROM).

The external input and output unit 160 serves as an interface with all external devices connected to the client terminal 100, and is used for direct or indirect connection to other external devices through communication or the like (for example, USB (Universal Serial Bus), IEEE1394, etc.) or a network (for example, a wireless local area network (LAN), Bluetooth (registered trademark), radio frequency identification (RFID), infrared communication (infrared Data Association: IrDA), ultra wideband (UWB) (registered trademark), or ZigBee (registered trademark)).

Examples of the external device connected to the client terminal 100 include a wired/wireless headset, a wired/wireless external charger, a wired/wireless data port, a memory card or a subscriber identity module (SIM) card/a user identity module (UIM) card connected via a card socket, an external audio and video device that is connected via an audio and video input/output (I/O) terminal, a wirelessly connected external audio and video device, a wiredly/wirelessly connected smartphone, a wiredly/wirelessly connected personal computer, a wiredly/wirelessly connected PDA (Personal Digital Assistant), and an earphone. The external input and output unit 160 may be configured to transfer data received a transmission from such an external device to each component in the client terminal 100 or transmit data in the client terminal 100 to the external device.

In response to an instruction of the main control unit 101, the GPS receiving unit 170 receives a GPS signal transmitted from GPS satellite ST1, and ST2 to STn, and executes a position measurement calculation process based on a plurality of received GPS signals to acquire position information specified by latitude, longitude, and altitude of the client terminal 100. When the GPS receiving unit 170 can acquire position information from the wireless communication unit 110 or the external input and output unit 160 (for example, a wireless LAN), the GPS receiving unit 170 can also detect the position using the position information.

The motion sensor unit 180 includes, for example, a three-axis acceleration sensor, and detects a physical motion of the client terminal 100 according to an instruction of the main control unit 101. By detecting the physical motion of the client terminal 100, a moving direction or an acceleration of the client terminal 100 is detected. The detection result is output to the main control unit 101.

The power supply unit 190 supplies power stored in a battery (not illustrated) to each unit of the client terminal 100 according to an instruction from the main control unit 101.

The main control unit 101 includes a microprocessor, operates according to a control program or control data stored in the storage unit 150, and integrally controls the respective units of the client terminal 100. Further, the main control unit 101 includes a mobile communication control function of controlling each unit of a communication system in order to perform voice communication or data communication via the wireless communication unit 110, and an application processing function.

The application processing function is realized by the main control unit 101 operating according to application software stored in the storage unit 150. Examples of the application processing function include an infrared communication function of controlling the external input and output unit 160 to perform data communication with a counterpart device, an electronic mail function of performing transmission and reception of an electronic mail, a web browsing function of browsing web pages, and a function of using the drug management system according to the present invention. The function of using the drug management system according to the present invention can be realized by downloading corresponding application software (hereinafter, referred to as "drug management program") from the cloud server 10 or thee site of the office that operates the drug management system 1.

Further, the main control unit 101 includes an image processing function of, for example, displaying an image on the display input unit 120 based on image data (data of a still image or a moving image) such as received data or downloaded streaming data.

Further, the main control unit 101 executes a display control for the display panel 121, and an operation detection control for detecting a user's operation through the operation unit 140 and the operation panel 122.

Through the execution of the display control, the main control unit 101 displays an icon for starting up application software or a software key such as a scroll bar, or displays a window for creating an electronic mail. The scroll bar refers to a software key for receiving an instruction to move a display portion of the image, for example, for a large image which cannot be fit to the display region of the display panel 121.

Further, through the execution of the operation detection control, the main control unit 101 detects a user's operation through the operation unit 140, receives an operation with respect to the icons through the operation panel 122 or an input of a character string to an input column of the window, or receives a request for scrolling of a display image through the scroll bar.

Further, through the execution of the operation detection control, the main control unit 101 includes a touch panel control function of determining an operating position with respect to the operation panel 122 is an overlapping portion (a display region) overlapping the display panel 121 or an outer edge portion (a non-display region) that does not overlap the display panel 121 other than the display region, and controlling a sensitive region of the operation panel 122 or a display position of the software key.

Further, the main control unit 101 can detect a gesture operation with respect to the operation panel 122, and execute a predetermined function according to the detected gesture operation. The gesture operation is not an existing simple touch operation and refers to an operation of drawing a trajectory using a finger or the like, simultaneously designating a plurality of positions, or combining them to draw a trajectory with respect to at least one of a plurality of positions.

Under the control of the main control unit 101, the camera unit 141 can convert image data acquired by imaging to compressed image data in a format of, for example, Joint Photographic coding Experts Group (JPEG) or the like and can record the image data in the storage unit 150 or can output the image data through the external input and output unit 160 or the wireless communication unit 110. In the client terminal 100, as illustrated in FIG. 16, although the camera unit 141 is mounted on the same surface as the display input unit 120, the mounting position of the camera unit 141 is not limited thereto, and the camera unit 141 may be mounted on a rear surface of the housing 102 instead of the surface of the housing 102 where the display input unit 120 is provided, or a plurality of camera units 141 may be mounted on the housing 102. In a case where the plurality of camera units 141 are mounted, the camera unit 141 used for imaging may be switched to perform imaging with a single camera unit 141, or a plurality of camera units 141 may be used simultaneously to perform imaging.

The camera unit 141 can be used for various functions of the client terminal 100. For example, an image acquired by the camera unit 141 can be displayed on the display panel 121, or an image acquired by the imaging of the camera unit 141 can be used as one operation input of the operation panel 122. In the example, the camera unit is used for reading a barcode (one-dimensional barcode or two-dimensional barcode) indicating the unique ID added to the packaging bag. In a case where the GPS receiving unit 170 detects the position, the position may be detected with reference to the image from the camera unit 141. In addition, the optical axis direction of the camera unit 141 of the client terminal 100 may be determined or a current use environment may be determined with reference to the image from the camera unit 141 without using the three-axis acceleration sensor or using the three-axis acceleration sensor. Of course, the image from the camera unit 141 can also be used within application software.

In addition, the position information acquired by the GPS receiving unit 170, the voice information (which may be text information acquired by voice text conversion of the main control unit or the like) acquired by the microphone 132, and data acquired by adding the posture information acquired by the motion sensor unit 180 to the image data of the still image or the moving image can be recorded in the storage unit 150 or can be output through the external input and output unit 160 or the wireless communication unit 110.

<Method of Acquiring Drug Information of Packaged Drugs>

When a hospital nurse distributes a packaged drug bag containing drugs prescribed for an inpatient at each administration time (after breakfast, after dinner, and the like), or when a person in charge of drug distribution at a long-term care health facility distributes a packaged drug bag to a resident in the long-term care health facility at each administration time, it is necessary to confirm whether the packaged drug bag to be distributed belongs to a recipient.

At this time, it can hardly be confirmed from the packaging bag whether the packaged drug bag to be distributed belongs to the recipient when a name of the recipient is not printed on the packaging bag. Further, even when the name of the recipient is printed on the packaging bag, if there are a plurality of recipients with the same name, distribution error of the packaged drugs can occur.

In addition, there may be a case where the nurse or the like wants to confirm a drug type of the packaged drugs contained in the packaging bag and so on. When information such as the drug type and so on are not printed on the packaging bag, the drug type of the packaged drugs and so on can hardly be easily confirmed from the shape or engraved marks of the drugs.

Further, this type of confirmation is not limited to the nurse and the person in charge of drug distribution, but the recipient or his/her family may want to confirm. Further, when some packaged drugs are left unused, there may be a need to confirm drug information such as a drug type of the packaged drugs and so on. For example, there may be a case where the unused packaged drugs are brought to a next hospital when the hospital is changed. A doctor or pharmacist at the next hospital may need to confirm drug information of the unused packaged drugs (the drugs have been taken so far) or determine whether the unused packaged drugs can be continuously administered. However, the drug information such as the drug type of the one-dose packaged drugs and so on can hardly be easily confirmed from the shape or engraved marks of the drugs.

On the other hand, using the drug management system 1 that unitarily manages the packaged drugs on a package basis, the nurse, the person in charge of drug distribution, the recipient, the pharmacist, and the doctor can easily acquire the drug information of the packaged drugs.

Figure 18:
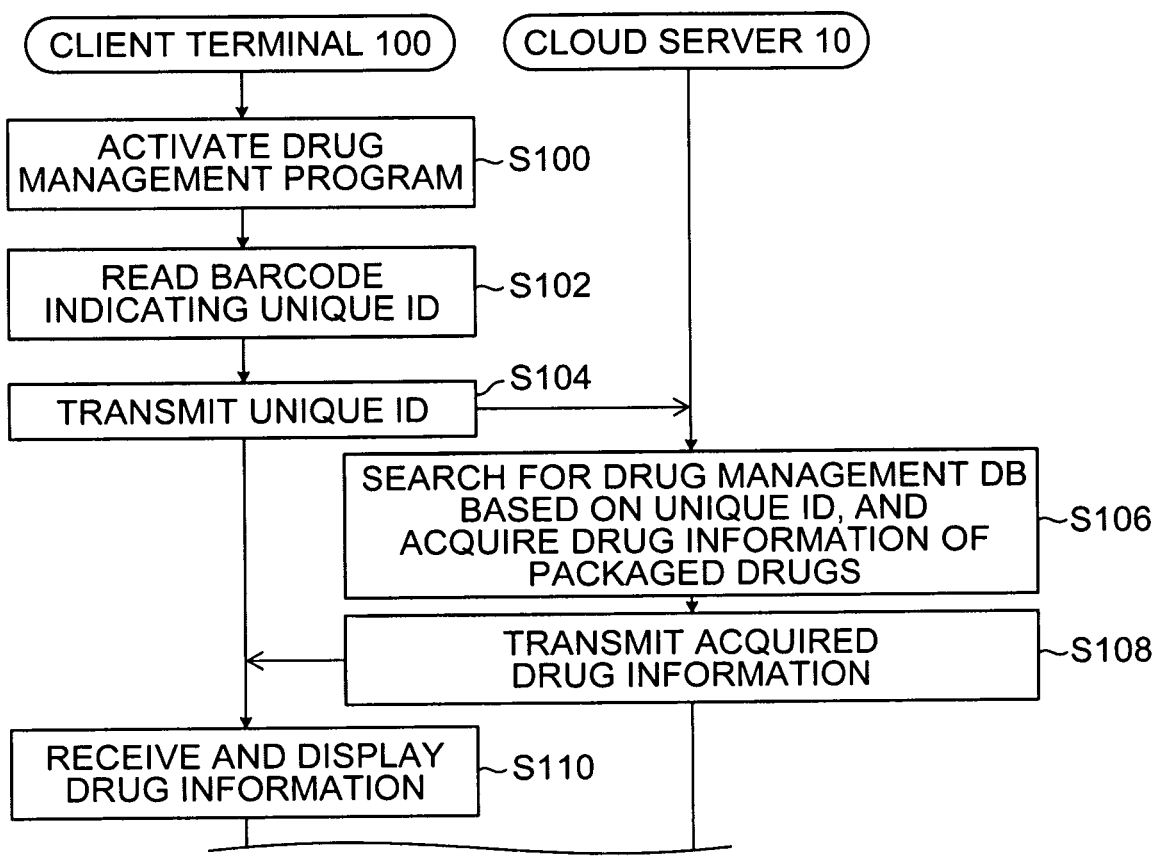
FIG. 18 is a flowchart illustrating an embodiment of a method of acquiring drug information of packaged drugs.

FIG. 18 is a flowchart illustrating an embodiment of a method of acquiring drug information of packaged drugs. Hereinafter, a case will be described in which a hospital nurse distributes packaged drugs to an impatient.

The nurse activates a drug management program of his/her client terminal 100 so as to use (get access to) the drug management system 1 (step S100).

The nurse takes an image of a barcode attached to the packaging bag containing the packaged drugs to be distributed to the impatient, using the camera unit 141 functioning as an information reading unit of the client terminal 100, and reads the barcode (unique ID indicated by the barcode) (step S102). The unique ID read by the client terminal 100 is transmitted to the cloud server 10 together with an acquisition request for the drug information of the packaged drugs according to the drug management program (step S104).

The cloud server 10, which has received the unique ID together with the acquisition request for the drug information of the packaged drugs, searches for the drug management DB based on the received unique ID and acquires the drug information of the packaged drugs managed in association with the unique ID (step S106). In addition to the drug information, prescription data such as a prescription date, patient information, or a drug administration time can be acquired.

The cloud server 10 transmits the drug information acquired based on the unique ID to the client terminal 100 which has sent the request (step S108).

The main control unit 101 and the wireless communication unit 110 functioning as drug information acquiring units of the client terminal 100 receive (acquire) the drug information of the packaged drugs and so on from the cloud server 10 according to the drug management program, and makes the display panel 121 of the client terminal 100 to display the received information (step S110). Thus, the nurse can confirm the drug information of the packaged drugs to be distributed and the information on the patient who takes the drug.

Although not illustrated in FIG. 18, a patient ID attached to a patient recognition wristband or a patient bed is read by the client terminal 100, patient information managed by a hospital server is acquired with the patient ID via a hospital LAN, and the patient information acquired from the cloud server 10 can be collated with the patient information acquired based on the patient ID attached to the patient recognition wristband or the like. Thus, the distribution of the packaged drugs by the nurse can be supported. That is, there is a management system for managing an administration error and an administration history by so-called "three-point authentication" in which a patient's wristband, a nurse's nameplate, and a drug label are read using the client terminal 100. In this embodiment, a barcode indicating a unique ID attached to the packaging bag can be read instead of the drug label.

In addition, the cloud server 10 can cooperate with an authentication server (not illustrated) to restrict browsing of the information on the packaged drugs from the user (accessor) of the client terminal 100 who access the cloud server 10. For example, when the user is a doctor or pharmacist, the cloud server 10 can allow the user to browse patient information, hospital information and pharmacy information, in addition to the drug information of the packaged drugs registered in association with the unique ID. When the user is a recipient, the cloud server 10 can allow the user to browse drug information and prescription date and prohibit the user to browse personal information (information of user himself/herself is permitted). Note that, the authentication of the doctor or pharmacist can be performed using, for example, a medical ID card such as HPKI (Healthcare Public Key Infrastructure) issued to health workers, thereby avoiding "impersonation".

Furthermore, it is preferable that, when uploading drug information of the packaged drugs and so on to the cloud server 10 in association with the unique ID, the pharmacists of the one or more facilities (pharmacies) 20 perform an electronic signature using, for example, an HPKI card to prove the uploaded drug information.

<Others>

The present embodiment is configured such that the drug management DB is established in the storage unit 14 provided in the cloud server 10, but is not limited thereto. For example, the drug management DB (for example, drug management DB related to packaged drugs which have been one-dose packaged at the facility) can be established in the storage unit of a PC (personal computer) of the one or more facilities (pharmacies) 20 so as to form a distributed DB, and the cloud server 10 may manage drug management DBs distributed in the one or more facilities as one drug management DB.

In addition, the system of the present embodiment can be configured to perform data cooperation between other cloud storage service systems such as a system which connects electronic medical charts, clinical examination values, examination images etc., via a network, regional health care cooperation, long-term care cooperation and so on, so as to mutually provide data.

Furthermore, the present embodiment is configured such that the unique identification information or the barcode indicating the unique identification information is printed on the packaging bag and the label printed with the unique identification information or the barcode indicating the unique identification information is attached to the packaging bag, but is not limited thereto. For example, the present embodiment may be configured such that the unique identification information is recorded on an electronic tag attached (embedded) to the packaging bag. In this case, it is preferable that the electronic tag is a write-once-read-many type memory which is capable of writing (writing of unique identification information) only once and thereafter only reading.

In the present embodiment, for example, the processors of the CPU 12 of the cloud server 10, the CPU 22A of the drug packaging apparatus 22-1, and the CPU 22A, the drug auditing unit 22F, and the numbering unit 22G of the drug package auditing apparatus 22-2 are various processors as described below in terms of hardware structure. The various processors include a central processing unit (CPU) that is general-purpose processor that executes software (program) to function as the processing units, a programmable logic device (PLD) that is a processor, such as an FPGA (field-programmable gate array), for which the circuit configuration can be changed after manufacturing, a dedicated electric circuit that is a processor, such as an ASIC (application-specific integrated circuit), having a circuit configuration specifically designed to perform a specific process, and so on.

One processing unit may be constituted by one of the various processors or a combination of two or more processors of the same type or different types (for example, a combination of a plurality of FPGAs or a combination of a CPU and an FPGA). Further, a plurality of processing units may be constituted by one processor. A first example configuration in which a plurality of processing units are constituted by one processor is a form in which one or more CPUs and software are combined to constitute one processor, and the processor functions as the plurality of processing units. A second example configuration is a form in which a processor that implements the functions of the entire system including the plurality of processing units with one IC chip is used, a representative example of the form is a system-on-a-chip (SoC). As described above, in terms of hardware structure, the processing units are constituted by one or more of the processors described above. Further, more specifically, in terms of hardware structure, these various processors are implemented as electric circuitry acquired by combining circuit devices, such as semiconductor devices.

In the present embodiment, the smartphone is described as an example of the client terminal 100, but is not limited thereto; for example, a tablet terminal, a mobile information terminal, and the like can be used.

Furthermore, the present invention is not limited to the above-described embodiments, and various modifications can be made without departing from the spirit of the present invention, as a matter of course.

REFERENCE SIGNS LIST

1: drug management system
2: network
10: cloud server
12, 22A, 22A-1: CPU
14: storage unit
16: numbering server
18: communication unit
20: one or more facilities (pharmacies)
22-1: drug packaging apparatus
22-2: drug package auditing apparatus
22-3: numbering device for drug packaging apparatus (numbering device)
22-4: drug packaging apparatus
22-5: one-dose packaged drug auditing apparatus
22B: drug packing unit
22C, 22C-1, 22C-2: communication unit
22D: label printer
22E: imaging unit
22F: drug auditing unit
22G: numbering unit
22H: printer
22I: display unit
22J: operation unit
24: receipt computer
26: LAN
40, 40-2: label
42, 42-2: character information
44: barcode
44-2: two-dimensional barcode
46, 46-2: patient's name
47, 47-2: drug administration time
48, 48-2: drug character information
50, 50-2: packaging bag
52, 52-2: drug
100: client terminal
101: main control unit
102: housing
110: wireless communication unit
120: display input unit
121: display panel
122: operation panel
130: calling unit
131: speaker
132: microphone
140: operation unit
141: camera unit
150: storage unit
151: internal storage unit
152: external storage unit
160: external input and output unit
170: GPS receiving unit
180: motion sensor unit
190: power supply unit
S10 to S110: step

What is claimed is:

1. A drug management system which unitarily manages packaged drugs packaged by a plurality of facilities, on a package basis, the drug management system comprising:
a cloud server including:
a cloud server processor; and a cloud server memory storing instructions, executable by the cloud server processor,
the cloud server processor configured to manage, in association with each other, unique identification information for uniquely specifying the packaged drugs on a package basis and drug information of the packaged drugs corresponding to at least the unique identification information;
a plurality of client terminals, each including a respective client terminal processor and a client terminal memory storing instructions, executable by the respective client terminal processor, each of the respective client terminal processors configured to access the cloud server;
a drug packaging apparatus provided to each of the plurality of facilities; and
a drug auditing unit configured to confirm whether the packaged drugs are drugs corresponding to prescription data,
wherein the drug packaging apparatus includes:
a drug packing device configured to receive the prescription data for each patient and put and package a plurality of drugs which include drugs whose drug types are different from each other and are to be taken in one dose by the patient according to the received prescription data in a packaging bag;
an information adding unit including a label printer configured to attach a label with the unique identification information to the packaging bag; and
a communication unit configured to upload at least the drug information of the packaged drugs contained in the packaging bag in association with the unique identification information, to the cloud server,
wherein the system includes a numbering unit provided in the cloud server or the drug packaging apparatus, and configured to issue the unique identification information;
wherein each client terminal processor of the plurality of client terminals is further configured to read the unique identification information on the packaging bag, and transmit the unique identification information to the cloud server,
when the cloud server receives the unique identification information added to the packaging bag from at least one of the plurality of client terminals accessing the cloud server, the cloud server transmits at least the drug information of the packaged drugs contained in the packaging bag based on the unique identification information, to the at least one of the plurality of client terminals,
the drug auditing unit is further configured to generate an audit image list including a list of a name, a drug master image, and a captured image of each of the packaged drugs contained in the packaging bag; and
the respective client terminal processor of the at least one of the plurality of client terminals is further configured to display the transmitted drug information of the packaged drugs contained in the packaging bag and the audit image list.

2. The drug management system according to claim 1, wherein
the information adding unit adds the unique identification information or a barcode indicating the unique identification information to the packaging bag; or attaches to the packaging bag, the label on which the unique identification information or the barcode indicating the unique identification information is added; or records the unique identification information on an electronic tag attached to the packaging bag.

3. The drug management system according to claim 1, wherein the information adding unit further adds, among patient information, a drug administration time and the drug information of the packaged drugs, at least the drug administration time to the packaging bag.

4. The drug management system according to claim 1, wherein the communication unit uploads information described in the prescription data in association with the unique identification information, to the cloud server, and the cloud server further manages the information described in the prescription data in association with the unique identification information.

5. The drug management system according to claim 1, comprising:

an imaging unit configured to capture an image of the packaged drugs before or after the drugs are put and packaged in the packaging bag;

wherein the drug auditing unit is further configured to support a pharmacist to confirm whether the packaged drugs are drugs corresponding to the prescription data based on the image of the packaged drugs captured by the imaging unit.

6. The drug management system according to claim 5, wherein when an instruction input indicating that audit of the packaged drugs is OK is received from the pharmacist by the drug packaging apparatus via an operation unit, the communication unit uploads, drug character or symbol information and the image used for audit in the drug auditing unit in association with the unique identification information, as the drug information of the packaged drugs, to the cloud server, and the cloud server manages the drug information and image of the packaged drugs in association with the unique identification information.

7. The drug management system according to claim 1, wherein each of the plurality of client terminals includes: an information reading unit configured to read the unique identification information added to the packaging bag; and a drug information acquiring unit configured to acquire, from the cloud server, at least the drug information of the packaged drugs contained in the packaging bag, based on the unique identification information read by the information reading unit.

8. The drug management system according to claim 1, wherein the unique identification information is a GS1 identification code.

9. A drug packaging apparatus provided to each of a plurality of facilities, the drug packaging apparatus comprising:

a drug packing device configured to receive prescription data for each patient and put and package a plurality of drugs which include drugs whose drug types are different from each other and are to be taken in one dose by the patient according to the received prescription data in a packaging bag;

a unique identification information acquiring unit configured to acquire, from a numbering unit configured to issue unique identification information for uniquely specifying packaged drugs packaged by the plurality of facilities on a package basis, the unique identification information;

an information adding unit including a label printer configured to attach a label with the unique identification information acquired by the unique identification information acquiring unit to the packaging bag; and a communication unit configured to upload at least drug information of the packaged drugs contained in the packaging bag in association with the unique identification information, to a cloud server including a cloud server processor, and a cloud server memory storing instructions, executable by the cloud server processor, the cloud server processor configured to unitarily manage the packaged drugs packaged by the plurality of facilities on a package basis, wherein when the cloud server receives the unique identification information added to the packaging bag from a respective client terminal processor of at least one of a plurality of client terminals accessing the cloud server, the cloud server transmits at least the drug information of the packaged drugs contained in the packaging bag based on the unique identification information, to the respective client terminal processor of the at least one of the plurality of client terminals, and the respective client terminal processor of the at least one of the plurality of client terminals is further configured to display the transmitted drug information of the packaged drugs contained in the packaging bag and an audit image list including a list of a name, a drug master image, and a captured image of each of the packaged drugs contained in the packaging bag.

10. A drug packaging apparatus provided to each of a plurality of facilities, the drug packaging apparatus comprising:

a drug packing device configured to receive prescription data for each patient and put and package a plurality of drugs which include drugs whose drug types are different from each other and are to be taken in one dose by the patient according to the received prescription data in a packaging bag; and a numbering device configured to issue unique identification information for uniquely specifying packaged drugs packaged by the drug packing device, on a package basis, wherein at least one of the drug packing device and the numbering device includes:

an information adding unit including a label printer configured to attach a label with the unique identification information to the packaged drugs packaged by the drug packing device, the unique identification information issued from the numbering device for the packaged drugs;

a communication unit configured to upload at least drug information of the packaged drugs contained in the packaging bag in association with the unique identification information, to a cloud server including a cloud server processor, and a cloud server memory storing instructions, executable by the cloud server processor, the cloud server processor configured to unitarily manage the packaged drugs packaged by the plurality of facilities on a package basis, wherein when the cloud server receives the unique identification information added to the packaging bag from a respective client terminal processor of at least one of a plurality of client terminals accessing the cloud server, the cloud server transmits at least the drug information of the packaged drugs contained in the packaging bag based on the unique identification information, to the respective client terminal processor of the at least one of the plurality of client terminals, and the respective client terminal processor of the at least one of the plurality of client terminals is further configured to display the transmitted drug information of the packaged drugs contained in the packaging bag and an audit image list including a list of a name, a drug master image, and a captured image of each of the packaged drugs contained in the packaging bag.

11. The drug packaging apparatus according to claim 9, wherein the information adding unit adds the unique identification information or a barcode indicating the unique identification information to the packaging bag, or attaches to the packaging bag, the label on which the unique identification information or the barcode indicating the unique identification information is added, or records the unique identification information on an electronic tag attached to the packaging bag.

12. The drug packaging apparatus according to claim 9, wherein the information adding unit further adds, among patient information, a drug administration time and the drug information of the packaged drugs, at least the drug administration time to the packaging bag.

13. The drug packaging apparatus according to claim 9, wherein the communication unit uploads the prescription data in association with the unique identification information, to the cloud server.

\* \* \* \* \*